(12) United States Patent
Chiou et al.

(10) Patent No.: US 8,470,597 B2
(45) Date of Patent: Jun. 25, 2013

(54) COMPOSITE FOR THERMO-SENSITIVE CELL-TISSUE TRANSPLANTED SCAFFOLD AND USE THEREOF

(75) Inventors: Shih-Hwa Chiou, Taipei (TW); Cherng-Kang Perng, Taipei (TW); Han-Tzo Lin, Taipei (TW); Yi-Ping Yang, Taipei (TW)

(73) Assignee: Taipei Veterans General Hospital, Taipei (TW)

( * ) Notice: Subject to any disclaimer, the term of this patent is extended or adjusted under 35 U.S.C. 154(b) by 191 days.

(21) Appl. No.: 13/008,760

(22) Filed: Jan. 18, 2011

(65) Prior Publication Data

US 2011/0159051 A1 Jun. 30, 2011

Related U.S. Application Data

(63) Continuation-in-part of application No. 11/742,963, filed on May 1, 2007, now abandoned.

(51) Int. Cl.
| | |
|---|---|
| *A61F 13/00* | (2006.01) |
| *C12N 5/0775* | (2010.01) |
| *C12N 5/07* | (2010.01) |
| *A61K 38/17* | (2006.01) |
| *A61L 15/32* | (2006.01) |

(52) U.S. Cl.
USPC ........... 435/325; 435/372; 424/447; 424/486; 442/123; 442/172; 427/2.31; 602/45; 602/54; 602/57; 530/354

(58) Field of Classification Search
None
See application file for complete search history.

(56) References Cited

U.S. PATENT DOCUMENTS

| | | | | |
|---|---|---|---|---|
| 5,595,756 | A | * | 1/1997 | Bally et al. .................... 424/450 |
| 6,022,330 | A | * | 2/2000 | Chen et al. ........................ 602/8 |
| 6,160,196 | A | * | 12/2000 | Knieler et al. .................. 602/48 |

OTHER PUBLICATIONS

Fu et al., "Enhanced wound-healing quality with bone marrow mesenchymal stem cells autografting after skin injury", Wound Repair and Regeneration 14: 325-335 (2006).*
Alhadlaq et al., "Mesenchymal stem cells: isolation and therapeutics", Stem Cells and Development 13: 436-448 (2004).*
Lin et al., "An animal study of a novel tri-layer wound dressing material—non-woven fabric grafted with N-isopropylacrylamide and gelatin", Mat. Chem. Phys. 64: 189-195 (2000).*
Morikawa et al., "Thermoresponsive artifical extracellular matrix: N-isopropylacrylamide-graft-copolymerized gelatin", J. Biomater. Sci. Polymer Edn. 13 (2): 167-183 (2002).*

* cited by examiner

*Primary Examiner* — Patricia A Leith
*Assistant Examiner* — Erin M. Bowers
(74) *Attorney, Agent, or Firm* — WPAT, P.C.; Anthony King

(57) ABSTRACT

A composite comprising a stem cell; a biodegradable layer, which can provide an environment for the stem cell to grow and to differentiate, and; a N-isopropylacrylamide (NIPAAm), which can polymerize with the biodegradable layer and possess the temperature-responsive character for easy stripping. The present invention further provides a method for treating a patient with a skin defect, consisting of (a) providing said patient with a composite consisting of a N-isopropylacrylamide (NIPAAm) layer polymerized with a biodegradable layer containing gelatin and a layer of polypropylene (PP) non-woven, wherein a bone marrow derived mononuclear cell with CD45 negative and glycophorin A negative is cultivating on the biodegradable layer; (b) covering said composite on the skin defect of the patient; and (c) treating the composite with water below 25° C. to strip off the layer of polypropylene (PP) non-woven.

4 Claims, 20 Drawing Sheets
(8 of 20 Drawing Sheet(s) Filed in Color)

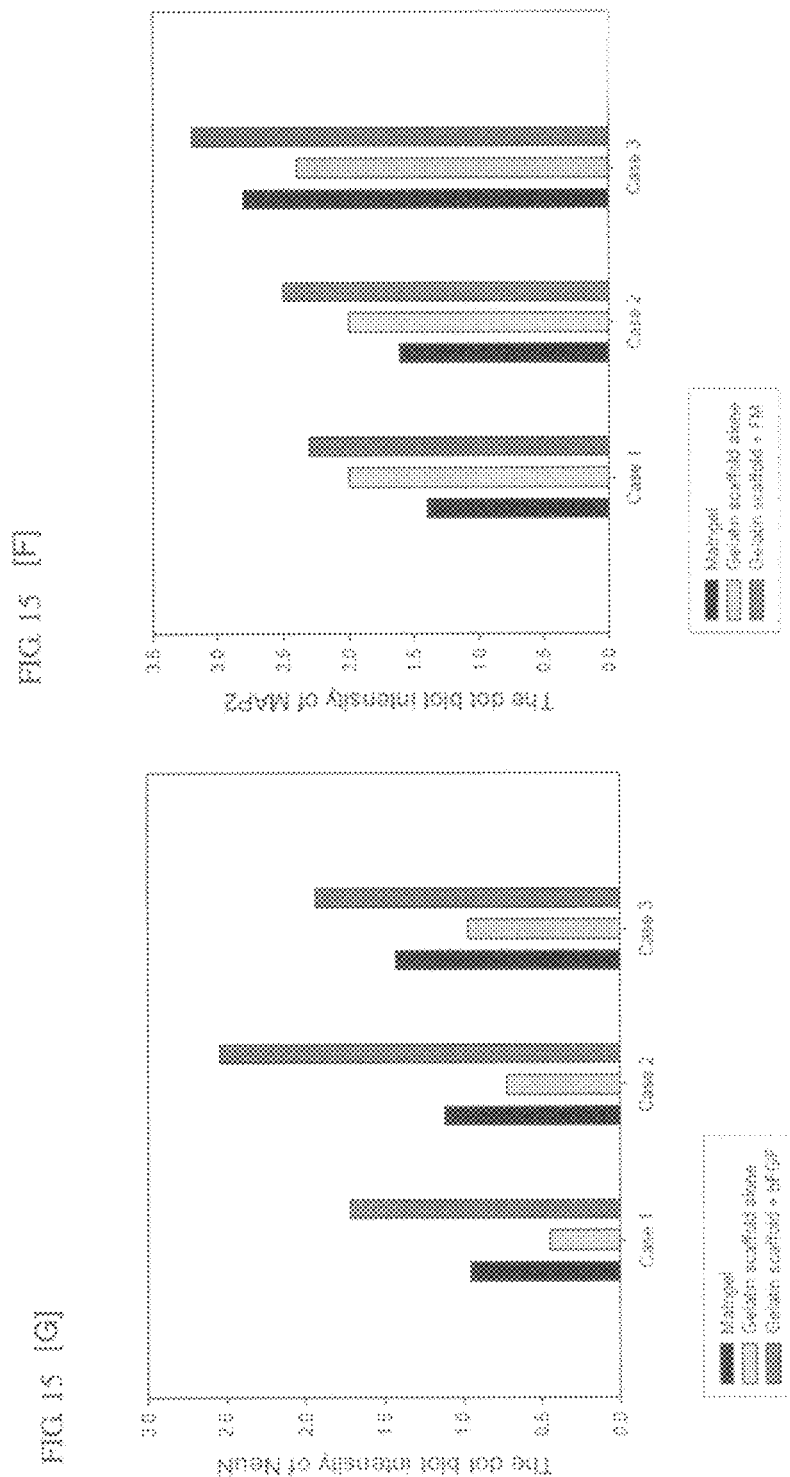

FIG.17 [B]
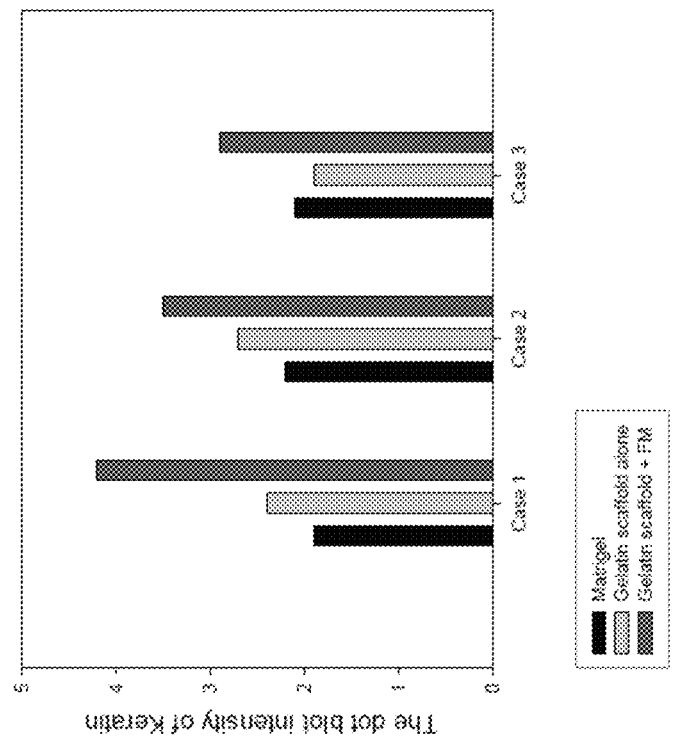
FIG.17 [C]
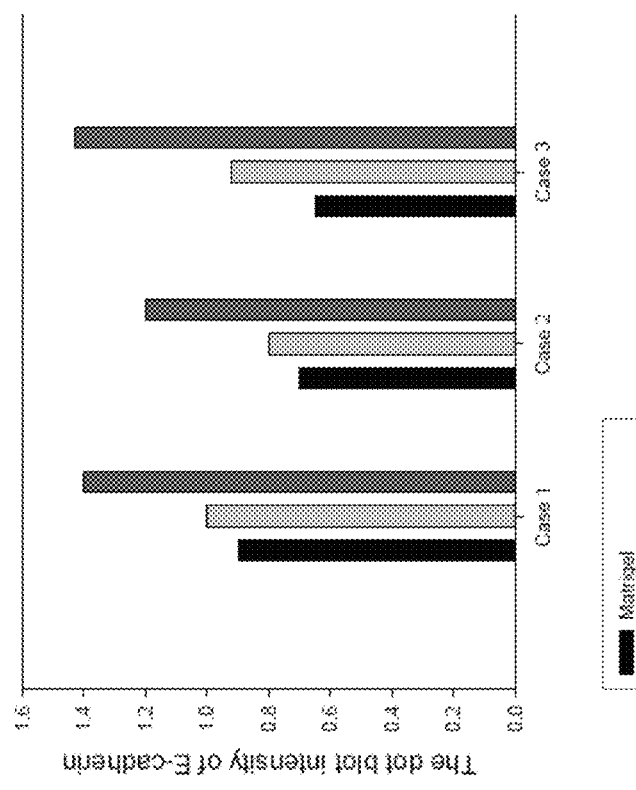

COMPOSITE FOR THERMO-SENSITIVE CELL-TISSUE TRANSPLANTED SCAFFOLD AND USE THEREOF

FIELD OF THE INVENTION

This invention relates to a method for treating a patient with a skin defect.

DESCRIPTION OF PRIOR ART

Skin is not just a passive barrier for fluid loss and mechanical injury but a complex organ in the human body. Skin injuries and defects may be caused by burn, trauma, cancer, or other diseases. For a small skin defect, primary or secondary healing is typically the simplest and most effective management. Autologous skin graft, however, is the standard treatment for large skin defects such as a major burn or trauma. The disadvantages of an autologous skin graft are possible donor site morbidity and the limitation of available skin amount especially in the case of subjects with extensive burns.

Skin tissue engineering is a possible solution for treating extensive skin defects. The ultimate goal of skin tissue engineering is to restore the complete functions of native skin, but until now the structures and functions of skins are only partially restored in known methods. Full-thickness skin regeneration by means of tissue engineering requires a material to restore the epidermal barrier function and dermal properties of mechanical stability and elasticity. The combination of cultivated keratinocytes and dermal substitutes in vitro is the current approach with variable success.

Scaffold-guided tissue regeneration involves seeding highly porous biodegradable scaffolds with donor cells and/or growth factors, then culturing and implanting the scaffolds to induce and direct the growth of new tissue. The goal is for the cells to attach to the scaffold, then replicate, differentiate (i.e., transform from a non-specific state into a cell exhibiting the functions of the target tissue), and organize into normal healthy tissue as the scaffold degrades. This method has been used to create various tissue analogs including skin, cartilage, bone, liver, nerve, vessels, etc. For example, donor bone cells have been cultured on hydroxyapatite (HA) ceramic scaffolds to create small-scale bone. This scaffold is prepared using sea coral. The microstructure of coralline HA is very similar to the mineralized component of natural bone ECM. The diameter of the pores in this structure is about 250 micrometers, or approximately three times the diameter of a human hair. While HA is osteogenic, there is still a need for better scaffolding materials which satisfy a range of goals related to strength, toughness, osetoinductivity, osteoconductivity, controlled degradation, and inflammatory response.

To date, only tissue engineered skin has been commercialized. There are still numerous issues to be addressed and challenges to overcome, for scaffold guided tissue generation to be extensible to the creation of more complex, large-scale structures. One key barrier is how to manufacture scaffolds that exhibit spatially controlled distributions of cells, growth factors, and scaffold materials and microstructures. Scaffold-based processes have limitations in addressing these needs due, in part, to restrictions of the manufacturing methods used to synthesize and seed scaffolds. Some of these limitations are summarized in the table below.

In recent years, temperature-responsive material such as thermoresponsive poly(N-isopropylacrylamide) (PNIPAAm) has been applied in tissue engineering. Harimoto M et al., disclosed a novel approach for achieving double-layered cell sheets co-culture in an article entitled: overlaying endothelial cell sheets onto monolayer hepatocytes utilizing temperature-responsive culture dishes (J Biomed Mater Res. 2002 Dec. 5; 62(3):464-70). Yamato M., et al., disclosed thermo-responsive culture dishes allow the intact harvest of multilayered keratinocyte sheets without dispase by reducing temperature (Tissue Eng. 2001 August; 7(4):473-80). Hsiue G. H. et. al., disclosed corneal endothelial reconstruction with a bioengineered cell sheet (Transplantation, 2006 Feb. 15; 81(3):473-6). (All of these references are herein incorporated by reference in their entirety.) However, the development of the above is still unsatisfied in commercialization due to their undesirable properties.

All referenced patents, applications and literatures are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply. The invention may seek to satisfy one or more of the above-mentioned desire. Although the present invention may obviate one or more of the above-mentioned desires, it should be understood that some aspects of the invention might not necessarily obviate them.

SUMMARY OF THE INVENTION

The present invention provides a composite comprising (a) a stem cell which differentiates into mature normal cell, osteocyte, chondrocyte, adipocyte, epithelium cell, epidermis-related cell, keratocyte, neuron, neural cell, insulin-positive cell, glucagons-positive cell, or tissues thereof; (b) a biodegradable layer for the stem cell to grow and differentiation, wherein the layer contains material selected from the group consisting of gelatin, fibronectin, collagen, laminin, bFGF, EGF, insulin, progesterone, glucose, SDF and thymosin beta-4; and (c) a N-isopropylacrylamide (NIPAAm), which polymerizes with the biodegradable layer to provide the feature of thermo-sensitive response for easy stripping.

This invention also provides a method for preparing a composite of the present invention comprising: (a) irradiating a NIPAAm solution with a UV light; (b) crosslinking the NIPAAm-grafted a cover in gelatin solution by the glutaraldehyde crosslinking agent; (c) freezing and drying the NIPAAm-grafted cover; (d) immersing the dried NIPAAm-grafted cover into the glutaraldehyde solution to produce a crosslinked gelatin hydrogel; (e) treating the crosslinked gelatin hydrogel with a glycine aqueous solution to block non-reacted aldehyde groups, and (f) cultivating a stem cell on the crosslinked gelatin hydrogel.

The present invention further provides a method for treating a patient with a skin defect, consisting of (a) providing said patient with a composite consisting of a N-isopropylacrylamide (NIPAAm) layer polymerized with a biodegradable layer containing gelatin and a layer of polypropylene (PP) non-woven, wherein a bone marrow derived mononuclear cell with CD45 negative and glycophorin A negative is cultivating on the biodegradable layer; (b) covering said composite on the skin defect of the patient; and (c) treating the composite with water below 25° C. to strip off the layer of polypropylene (PP) non-woven.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
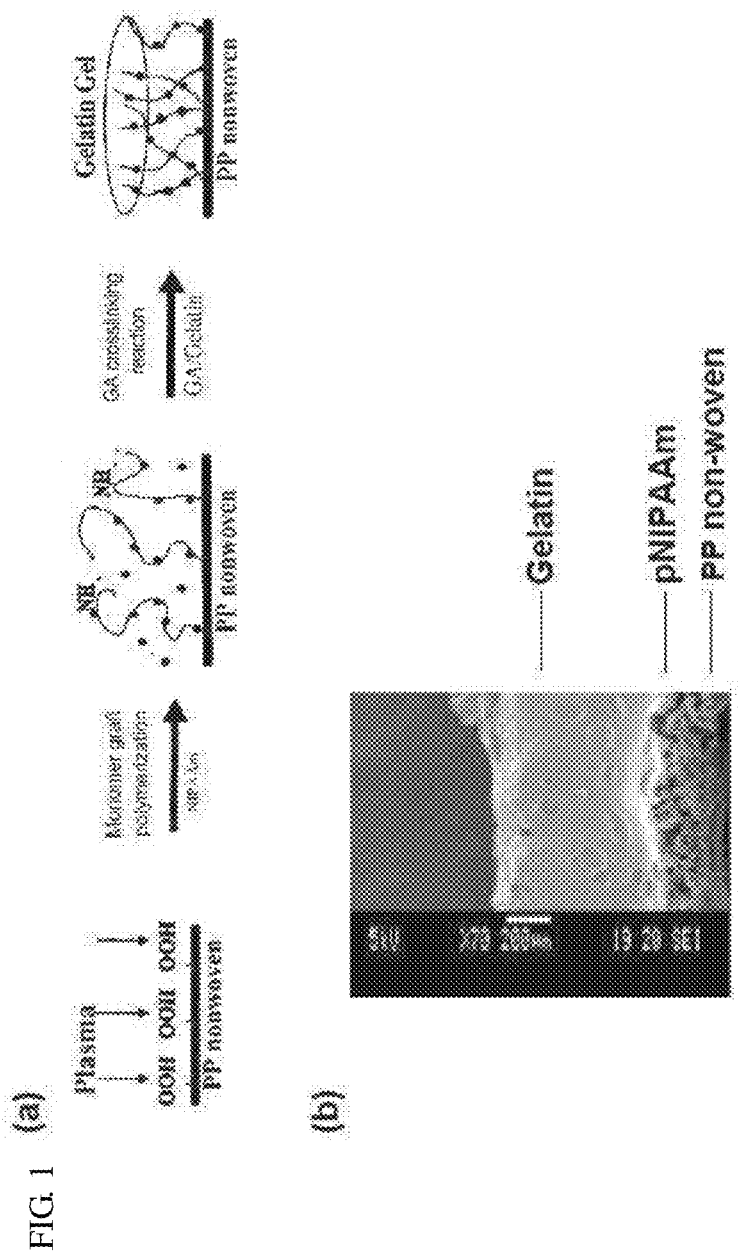
FIG. 1 shows (a) schematic diagram of the chemical reaction of surface immobilized gelatin, plasma activation, PNIPAAm graft-polymerization, and gelatin immobilize on PNIPAAm by GA crosslink agent. (b) Scanning electrical microscope (SEM) study showed the composite of the trilayer (gelatin/PNIPAAm/PP non-woven) cell-transferred scaffold after freeze-dried. (c) the flow chart of preparing the composite of the present invention. VOL: Ventilation outer layer, ESI: Easy striped (NiPPAm) interface. (d) the illustration of crosslinking gelatin with collagen fiber.

Recently, mesenchymal stem cells (MSC) or stromal cells, derived from the human bone marrow, can be purified and cultivated based on their self-renewal ability to adhere to plastic and differentiate into connective tissue lineages of mesodermal—osteocyte, chondrocyte, and adipocyte. Adult human bone marrow stem cells (hBMSCs) that are of multi-lineaged potential and showed the ability to differentiate can be cultivated into cell types of all three germ layers. Moreover, the present invention also established a biomaterial system to transfer skin and keratocyte with temperature-sensitive materials. In this invention, the differentiation potential of epidermis and the capability of skin wound healing were investigated, and the green fluorescence protein (GFP) gene was transduced into the hBMSCs by using the murine stem cell viral vector. The GFP-labeled hBMSCs were then cultured on the gelatin scaffold with the polypropylene non-woven N-isopropylacrylamide (pNIPAAm), and the GFP signals in the healing processes of skin-defect animal model were further monitored. This novel method provided a transferred system for cell therapy and while maintaining its temperature-sensitive property and the ease of peeling by lower-temperature treatment.

Accordingly, the present invention provides a composite comprising:
(a) a stem cell which differentiates into mature normal cell, osteocyte, chondrocyte, adipocyte, epithelium cell, epidermis-related cell, keratocyte, neuron, neuronal cell, insulin-positive cell, or tissues thereof;
(b) a biodegradable layer for the stem cell to grow and differentiation, wherein the layer contains material selected from the group consisting of gelatin, fibronectin, collagen, laminin, bFGF, EGF, insulin, progesterone, glucose, SDF and thymosin beta-4; and
(c) a N-isopropylacrylamide (NIPAAm), which polymerizes with the biodegradable layer to provide the feature of thermo-sensitive response for easy stripping.

In the present invention, the stem cell can differentiate into mature normal cell, osteocyte, chondrocyte, adipocyte, epithelium cell, epidermis-related cell, keratocyte, neuron, neuronal cell, insulin-positive cell, or tissues thereof. In the preferred embodiment, the stem cell is selected from the group consisting of (a) adult stem cell derived from bone marrow, umbilical tissues, or placenta; (b) neural stem cell; and (c) embryonic stem cell.

In the present invention, the biodegradable layer contains material selected from the group consisting of gelatin, fibronectin, collagen, laminin, bFGF, EGF, insulin, progesterone, glucose, SDF and thymosin beta-4. The preferred embodiment of the layer contains gelatin, fibronectin or collagen type 1. In the preferred embodiment of the layer contains gelatin or collagen type 1.

The formulated medium (FM) used for different stem cells is illustrated in Table I.

TABLE I the formulated medium (FM) used in the present invention

| Type of stem cells | Formulated medium (FM) in scaffold |
|---|---|
| Bone marrow mesenchymal stem cells | DMEM medium, gelatin (5%), fibronectin (1%), collagen (1%), laminin (1%), bFGF (10 ng/ml), thymosin (10 ng/ml), SDF (10 ng/ml), 10% fetal calf serum or human serum |
| Dermis derived mesenchymal stem cells | DMEM medium, gelatin (5%), fibronectin (1%), collagen (1%), laminin (1%), bFGF (10 ng/ml), EGF (10 ng/ml), SDF (10 ng/ml), 10% fetal calf serum or human serum |
| neuron stem cells | DMEM/F12, bFGF (10 ng), serum free |
| pancreatic | DMEM/F12, insulin (100 ug/ml), transferrin |

TABLE I-continued the formulated medium (FM) used in the present invention

| Type of stem cells | Formulated medium (FM) in scaffold |
|---|---|
| stem cells | (20 nmol/L), progesteron (60 umol/L), glucose 25 ug/ml, 10% Fetal calf serum |

To facilitate performing the peeling action and to protect the composite of the present invention, the N-isopropylacrylamide (NIPAAm) can further polymerize with a cover to form a protective layer. In a preferred embodiment, the cover is PP non-woven.

The present invention further provides a method for preparing a composite of the present invention comprising:
(a) irradiating a NIPAAm solution with a UV light;
(b) crosslinking the NIPAAm-grafted a cover in gelatin solution by glutaraldehyde crosslinking agent;
(c) freezing and drying the NIPAAm-grafted cover;
(d) immersing the dried NIPAAm-grafted cover into the glutaraldehyde solution to produce a crosslinked gelatin hydrogel;
(e) treating the crosslinked gelatin hydrogel with a glycine aqueous solution to block non-reacted aldehyde groups, and;
(f) cultivating a stem cell on the crosslinked gelatin hydrogel.

In a preferred embodiment of the present invention, the UV light is 50-2000 W UV light. In a more preferred embodiment of the present invention, the UV light is 100-500 UV light. In a further more preferred embodiment of the present invention, the UV light is 150-250 UV light.

NIPAAm-grafted PP non-woven in step (c) is dried out. To further remove non-reacted aldehyde groups, the method of present invention further washes with the double-distilled water after step (e).

The present invention further provides a method of treating a subject with a skin defect, the method comprises covering the composite of the present invention on the skin defect of the subject in need of such treatment.

The present invention further provides a method treating a patient with a skin defect, consisting of: (a) providing said patient with a composite consisting of a N-isopropylacrylamide (NIPAAm) layer polymerized with a biodegradable layer containing gelatin and a layer of polypropylene (PP) non-woven, wherein a bone marrow derived mononuclear cell with CD45 negative and glycophorin A negative is cultivating on the biodegradable layer; (b) covering said composite on the skin defect of the patient; and (c) treating the composite with water below 25° C. to strip off the layer of polypropylene (PP) non-woven, wherein the composite is covered on the skin defect of the patient for 3 to 21 days. The skin defect of the present invention is a wound resulted from trauma or burn injury. The bone marrow derived mononuclear cell with CD45 negative and glycophorin A negative of the present invention has the capacity to give rise to epithelium, connect tissue and small vessels. And the bone marrow derived mononuclear cell of the present invention is cultivated on the biodegradable layer for 2 to 3 weeks.

The term "skin defect" used herein includes, but not limited to, burn, trauma or wound. In a preferred embodiment, the wound is resulted from surgery or burn.

To facilitate performing the peeling action and to protect the composite of the present invention, the N-isopropylacrylamide (NIPAAm) can further polymerize with a cover to form a protective layer. In a preferred embodiment, the cover is PP non-woven. The cover is easily peeled by treating under room temperature (such as 25° C.) on the cover.

The term "subject" used herein includes, but not limited to, an animal. In a preferred embodiment, the subject is a mammal. In a more preferred embodiment, the subject is a human.

The present invention further provides a method of monitoring cell growth or tissue engineering in an animal, the method comprises applying the composite to the animal in need of such monitoring, wherein the composite comprises a stem cell labeled by a marker; a biodegradable layer, which can provide an environment for the stem cell to grow, differentiate, and; a N-isopropylacrylamide (NIPAAm), which can polymerize with the biodegradable layer.

The monitoring method of the present invention can be applied to monitor cell development or tissue engineering in an animal under in vitro or in vivo condition. In the preferred embodiment, the monitoring method can monitor development induction of skin-related, pancreas islet-related cells (such as like insulin- and glucagon-positive cells), neural cell, or neurons.

The marker used herein includes, but not limited to, a fluorescent protein gene such as green, red or blue fluorescent protein.

EXAMPLE

The examples below are non-limiting and are merely representative of various aspects and features of the present invention.

Example 1

Materials and Methods

Preparation of Easy-Peeling Scaffold

Polypropylene (PP) non-woven was cut into strips (2×3 cm$^2$) and washed in distilled water and the 95% ethanol solution. The N-isopropylacrylamide (NIPAAm) was supplied by Eastman Kodak Co. Ltd USA; the ammonium persulfate (APS) was purchased from Wako Pure Chemical Industry Co., Ltd. The N,N,N',N'-tetra-methylethylene-diamine (TEMED) was purchased from Fluka and N,N'-methylene-bis-acrylamide (NMBA) from Sigma. Other agents or drugs were all of chemical grade. The PP nonwoven was placed into a plasma treatment system with a rotating substrate holder. Then the graft polymerization of the 10 wt % NIPAAm solution was carried out with a 1000 W UV light irradiated for 30 minutes. The NIPAAm-grafted PP non-woven was chemically crosslinked in gelatin solution by the GA crosslinking agent. The NIPAAm-grafted PP non-woven was placed into a −80° C. refrigerator for three hours and further placed into a freeze-dryer for 1~2 days to completely dry the sample. Finally, the dry sample was immersed into the glutaraldehyde solution to process the crosslinking reaction overnight. After that, the crosslinked gelatin hydrogel was further treated with the 0.1 M glycine aqueous solution to block the non-reacted aldehyde groups, and then washed three times with the double-distilled water. The preparation was illustrated in FIGS. 1 (a) and (c).

Easy-Peeling Scaffold Property Evaluation

Swelling behavior of the hydrogel in the distilled water was observed and measured by the soaking weight variation in a temperature-controlled water bath. The temperature of the water bath was adjusted within 10~50° C. The swelling ratio was calculated according to the following equation:

Swelling ratio=$(Ws-W0)/W0$ where W0 and Ws indicated weights of dried and swollen samples respectively. The strip-off strength of pNIPAAm hydrogel was tested by using the elongation machine (NEXYGEN). Samples were tightly clipped by the clamping apparatus which was placed on both sides of the samples.

Bone Marrow Stem Cells Culture

The Declaration of Helsinki was used and has been reviewed by the Institutional Review Committee at Taipei Veterans General Hospital. The bone marrow (BM) was obtained from 5 healthy adult donors following informed consents (ages 17 to 63). The BM mononuclear cells (MNC) were obtained by Ficoll-Paque density gradient centrifugation (Lymphoprep, 1.073 g/ml; Sigma). Cells (5×10$^5$) obtained from the BM MNCs were negative for CD45 and glycophorin A after depletion of CD45$^+$ and glycophorin A$^+$ cells by micromagnetic beads (MACS, Stem Cell Technologies). These cells were then plated in the human fibronectin (FN)-coated (5 ng/ml, Sigma) 96-well plates. The expansion medium consisted of Dulbecco's modified Eagle's medium with 1 g/l of glucose (DMEM-LG, Gibco) and 10% fetal bovine serum (FBS; Gibco) supplemented with 10 ng/ml bFGF, 10 ng/ml EGF, 10 ng/ml PDGF-BB (R&D), 100 units/ml penicillin, and 1,000 μg/ml streptomycin, and 2 mM L-glutamine (Gibco). Once the adherent cells were more than 50% confluent, they were removed with the 0.25% trypsin-EDTA (Sigma) and replated at a 1:3 dilution under the same culture condition. The cell densities were maintained between 1×10$^3$ and 3×10$^3$ cells/cm$^2$.

Immunophenotypic Analysis.

For the hBMSC cell surface antigen phenotyping, sixth- to eighth-passage cells were detached and stained with anti-CD13 (Chemicon), CD34 (Chemicon), CD44 (Chemicon), CD45 (Chemicon), CD49b (Chemicon), CD81 (Chemicon), AC133 (Chemicon), SH2, SH3 (DAKO), and secondary fluorescein (FITC)- or phycoerythrin (PE)-coupled antibodies (Chemicon). The hBMSCs were fixed with 2% paraformaldehyde until analysis using the FACSCalibur apparatus (Becton Dickinson).

GFP Gene Delivery by MSCV Retrovirus

The cDNA plasmids of MIGFP, PMD, and VZV-G of murine stem cell retroviral vectors (MSCV; a gift from Shih C C and Yee J K; City of Hope, Duarte, Calif., USA) have been described previously. To generate the GFP retroviral supernatants, 293 cells were transiently transfected by calcium phosphate-mediated coprecipitation with 5μg of the plasmids. The cells were fed at the 24$^{th}$ hour with postinfection, and the retroviral supernatant was used at the 48$^{th}$ hour. The cell continued to produce high-titer retrovirus for another 2 days. Supernatant was used if needed for additional experiments. The supernatant was collected, brought to 8 ng of polybrene per ml-10 mM HEPES, and filtered with a 0.45 μm pore-sized filter. The hBMSC cells for infection were washed and trypsinized. They then were plated at 10$^6$ cells per well of a six-well dish and centrifuged. The medium was removed, and the retroviral supernatant was added at 1 ml/10$^6$ cells.

Animal Study and In Vivo GFP Imaging

The animal experiment followed and obeyed the "Principles of laboratory animal care" of Taipei Veterans General Hospital and National Yang-Ming University. After anaesthetizing with the 40 mg/kg pentobarbital intraperitoneal injection, a circular skin defect with a 2-cm diameter including panniculous carnosus was created on the back skin of the nude mice (8 w/o). The defect was covered by the scaffold with the hBMSC cultured in vitro for 2 to 3 weeks and surrounded by a plastic ring to prevent epithelialization to adjacent skin. The hBMSC group mice also received the in vivo GFP imaging evaluation. The excitation filter of 470 nm with a lamp supply of optical lighting of 150 watts (Southern California Services, USA) was used as an excited light source (470 nm) to project on the foci of the GFP-positive cells of the living mice and ex vivo transplanted tissues. The GFP imaging capture and photography were based on the record of the digital camera (Olympus) through optical configuration of dissected microscope (SZ60; Olympus) with a 515 nm viewing (emission) filter. The growth size of the xenografts was plotted and analyzed with the software of Image-Pro Plus (Media Cybernetics, USA).

Western Blot Assay

The scaffolds with hBMSCs at the skin defect were harvested at days 0, 7, 14, and 21 day of post-transplantation. The cell lysates were prepared as described. Fifteen μL of the sample was boiled at 95° C. for 5 minutes and separated on a 10% SDS-PAGE. The proteins were transferred to a Hybond-ECL Nitrocellulose paper (Amersham) by the wet-transfer system. The monoclonal antibodies (mAB) used to identify protein products were anti-human cytokeratin mAB (Chemicon), anti-human E-cadherin mAB (Chemicon), anti-human CD13 mAB (Chemicon), anti-human CD105 mAB (Chemicon), and anti-β-actin mAB (Chemicon). The reactive protein bands were detected by the ECL detection system (Amersham).

Statistical Analysis

Statistical analysis was performed by using the ANOVA test. The results were reported as mean±SD. A $p<0.05$ was considered to be statistically significant.

Example 2

Easy-Peeling Scaffold Property Evaluation

Figure 2:
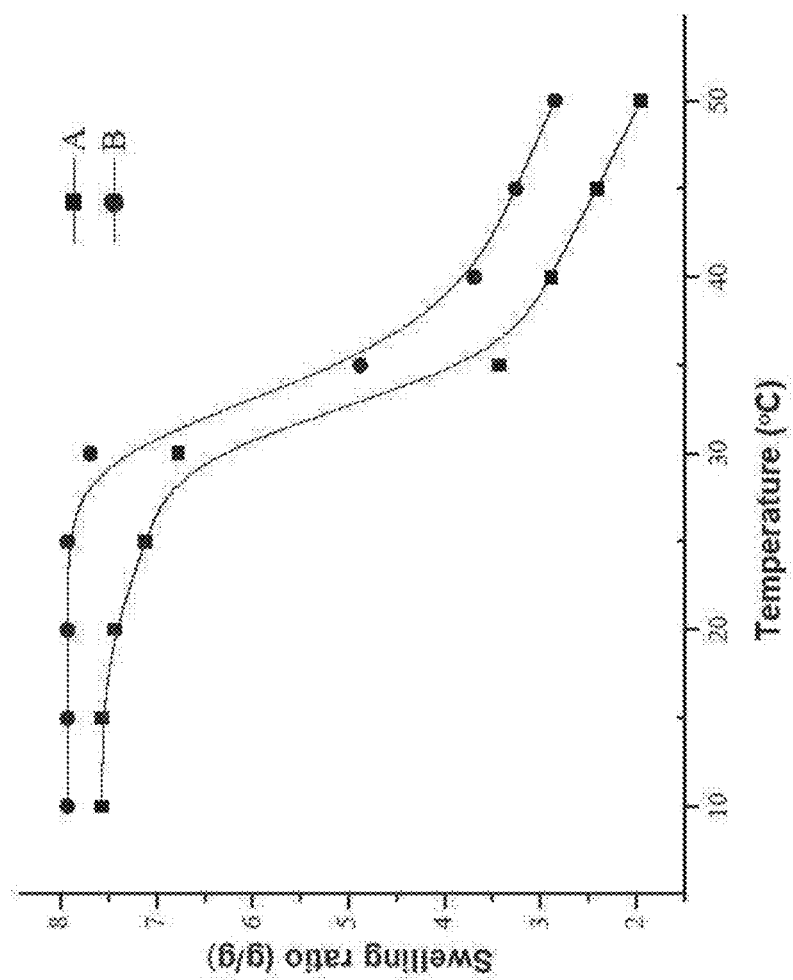
FIG. 2 shows the effects of temperature variation on swelling ratio of the tested hydrogel. (● solid circle: Pure PNIPAAm hydrogel, ■ solid square: The trilayer cell-transferred scaffold).

As showed in FIG. 1 (b), the composite of the trilayer (gelatin/pNIPAAm/PP non-woven) cell-transferred scaffold was demonstrated by scanning electrical microscope. As showed in FIG. 2, the thermo-sensitive response behavior and swelling ratio variation between the pure pNIPAAm hydrogel and the trilayer scaffold showed a similar trend. Furthermore, they all revealed the equivalent lower critical solution temperature (LCST) point at around 32° C. It demonstrated that the pNIPAAm hydrogel exhibited its temperature-sensitive property even if it was grafted onto the surface of different substrates. The trilayer scaffold after the freeze-dried treatment exhibited the higher force (57 Newton) for PP mesh being separated from the scaffold. When immersed this composite in room-temperature water for 2-3 hours to the swelling state, the strip-off force decreased to 1 Newton. However, when it was put in hot water (>34° C.), the force increased to 7 Newton (Table II). The result showed that the PP membrane could attach to the gelatin scaffold firmly when applied to skin defects when the body temperature is around 37° C. After the scaffold was healed to the wound bed, the PP membrane could be easily stripped off by the lower-temperature treatment

TABLE II

The stripped strength of pNIPAAm composites at different elongation state

| Status | Average stripped force (N) |
|---|---|
| Freeze-Dried | 57.36 ± 3.07 |
| Swelled at low-temperature (<25° C.) | 1.27 ± 0.21 |
| Swelled at high-temperature (>34° C.) | 7.28 ± 0.36 |

Example 3

Bone Marrow Stem Cells (BMSCs) Culture

Figure 3:
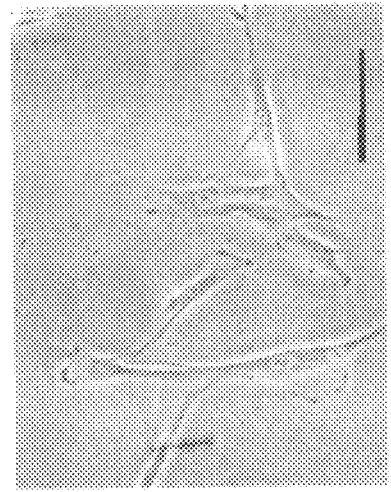
FIG. 3 shows isolation and Characteristic of adult human bone marrow stem cells (hBMSCs). (a) hBMSCs were isolated and usually appeared as spindle-shaped cells (bar: 30 μm). (b) BMSCs were cultured for 10th passage and labeled with monoclonal antibodies of CD45, CD34, AC133, CD13, CD49b, CD105, CD81, SH3, and SH4 for by FACS analysis.
Figure 3:
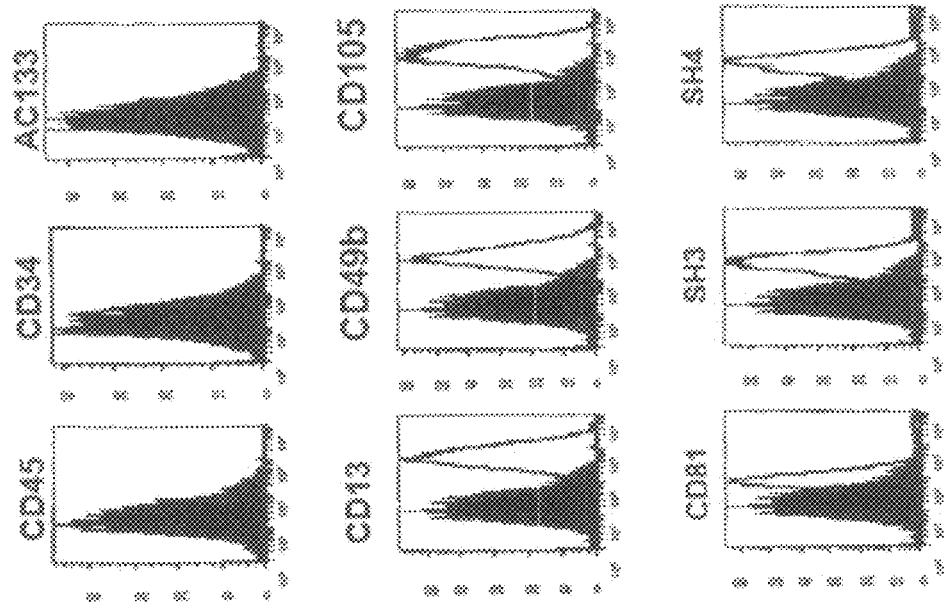
Figure 4:
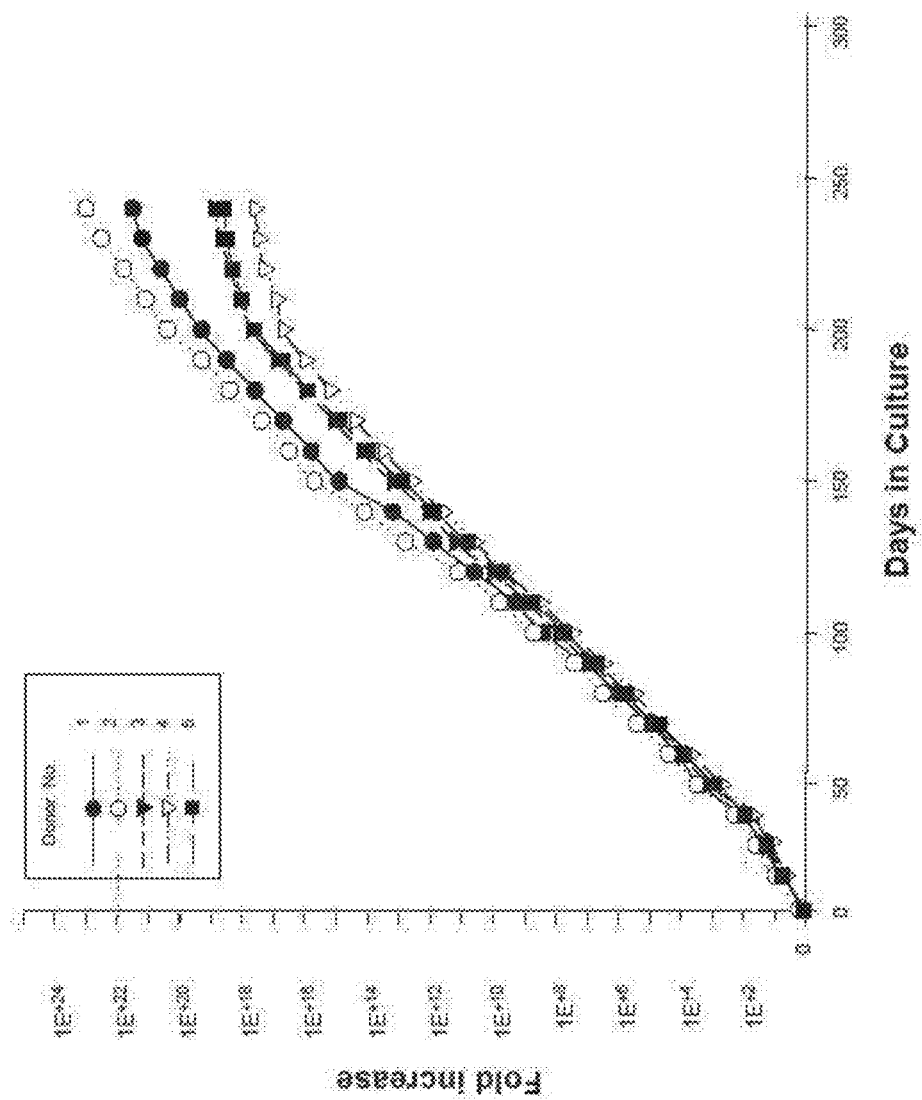
FIG. 4 shows the cell growth and proliferation rate of hBMSCs in the different passage. The hBMSCs isolated from 5 different donors were expanded in vitro and passaged every 7 days for more than 30 passages.

As showed in FIG. 3(a), the protocol for isolating the hBMSCs from fresh human BM of five donors was used. hBMSCs usually appeared as spindle-shaped cells with scant cytoplasm and had granules around the nuclei. Within 7 days, the cultures of hBMSCs were nearly confluent and were passaged at 1:3. As showed in FIG. 3(b), the flow cytometry analysis revealed that the hBMSCs were strongly positive for CD13, CD49b, CD105, CD81, SH3, and SH4, but negative for CD45, CD34, and AC133. As showed in FIG. 4, the hBMSC morphology and phenotype remained unchanged for more than 30 cell passages [n=5]. To further monitor the tumor cell proliferation in vitro and in vivo, GFP gene was transduced into hBMSCs using MSCV. As showed in FIG. 5(a), the GFP-positive hBMSCs (hBMSCs-GFP) were then sorted by flow cytometry. The hBMSCs-GFP stably passaged and expressed the markers of mesenchymal stem cells to $30^{th}$ passage (Table III).

TABLE III

The percentage of immunophenotypically positive MSCs at different passages

|  | P5 | P10 | P15 | P20 | P25 | P30 |
|---|---|---|---|---|---|---|
| CD13 | 90% | 88% | 92% | 91% | 87% | 85% |
| CD49b | 87% | 86% | 88% | 87% | 85% | 86% |
| CD105 | 89% | 85% | 84% | 90% | 87% | 88% |
| CD34 | 0.5% | 0% | 0.3% | 0% | 0.5% | 0.2% |
| CD45 | 0% | 1% | 0% | 0.5% | 1% | 0.5% |

P: cell passage

Example 4

In Vitro Culture of GFP-Labeled hBMSC on the Easy-Peeling Scaffold

Figure 5:
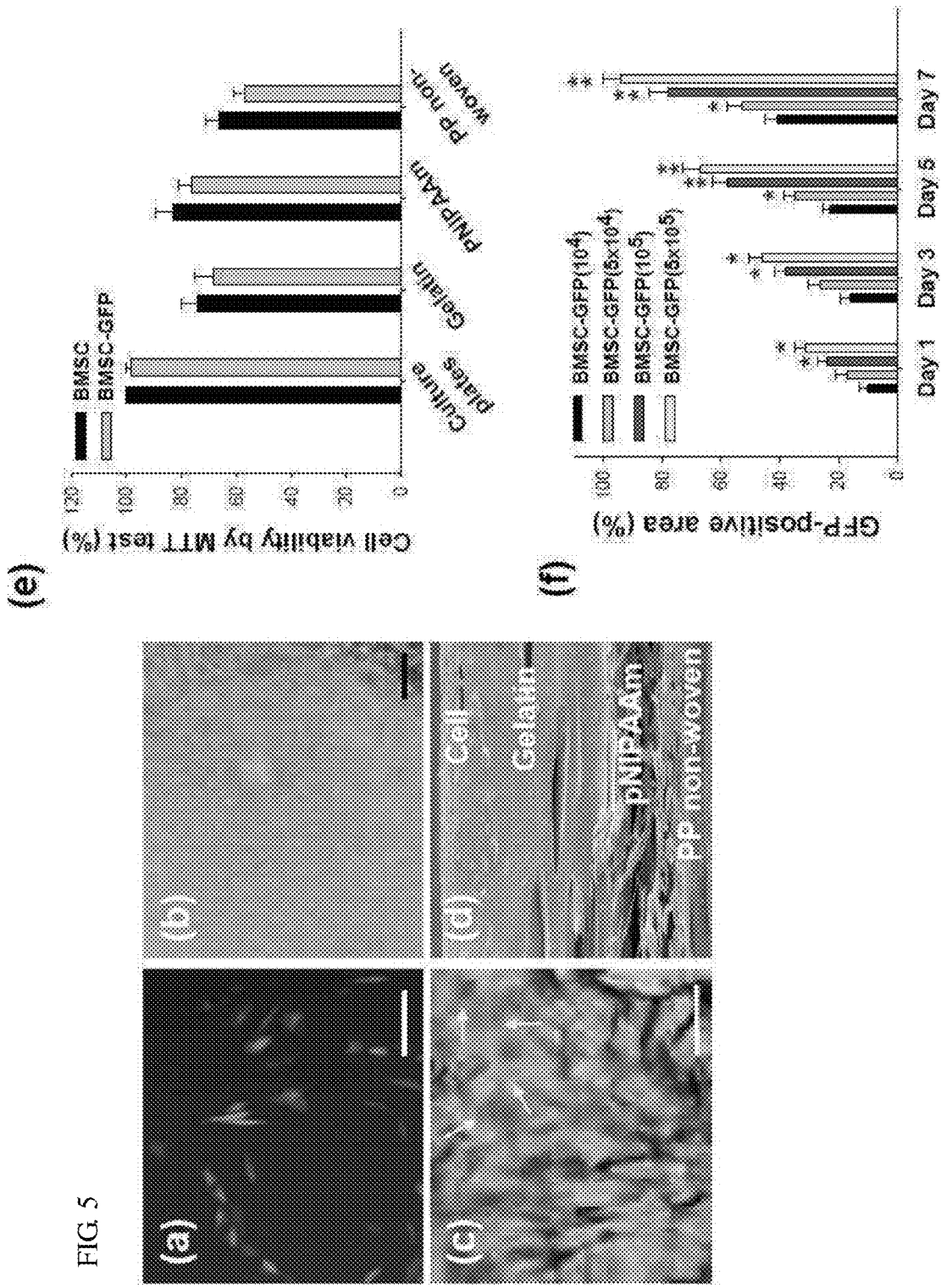
FIG. 5 shows (a) the GFP-positive hBMSC cells were detected by in vitro GFP imaging system. (b) BMSCs-GFP was cultured on gelatin scaffold with pNIPAAm. (c) hBMSCs were found in the gelatin scaffold by the H&E stain. Arrows: the tight conjunctions of cell-to-cell (bar: 50 μm). (d) The longitudinal section of the multi-layer adult human bone marrow stem cell-transferred scaffold by SEM. (e) The cell viability of hBMSCs-GFP cultured on gelatin scaffold with pNIPAAm. (f) The elevation of growth rate of hBMSCs-GFP on gelatin scaffold with pNIPAAm by in vitro GFP imaging system. (*: $p<0.05$; **: $p<0.01$ compared with $10^4$ BMSC-GFP).

To further develop an easy-peeling scaffold with the adult human bone marrow stem cells, the hBMSCs-GFP was cultivated by using temperature-responsive culture surface-gelatin/pNIPAAm. By using in vitro GFP imaging system, the results indicated in FIGS. 5(b) and 5(f) showed that $5 \times 10^5$ hBMSCs-GFP can grow and become confluent on the gelatin scaffold (3.14 cm$^2$) with pNIPAAm after 7 day culture. The histological study indicated in FIG. 5(c) showed that hBMSC-GFP can attach at gelatin scaffold with pNIPAAm. As showed in FIG. 5(d), the longitudinal section of SEM study further revealed that the multi-layer structure of hBMSC-transferred membrane (hBMSC/gelatin scaffold with pNIPAAm) could be formed and exhibit the whole integrity for transplanted manipulation. Furthermore, the cell viability and proliferation of hBMSCs-GFP were analyzed by using MTT reduction assay. As showed in FIG. 5(e), there were no significant difference between hBMSC group and hBMSC-GFP group [$p>0.05$].

Example 5

Animal Study and In Vivo GFP Imaging

Figure 6:
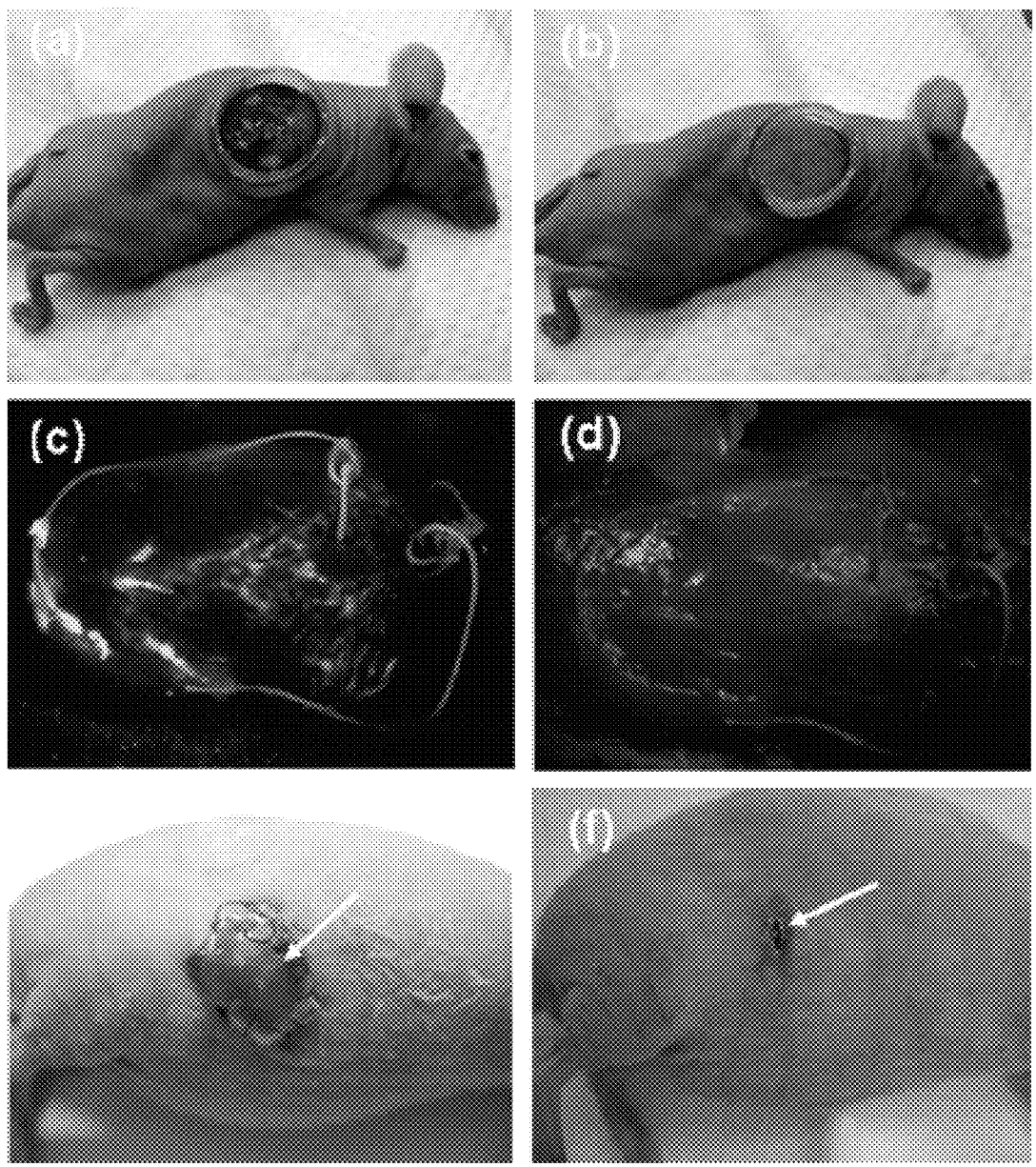
FIG. 6 shows determination of (a-f) wound size and (c, d) the growth rate of hBMSCs-GFP in skin-defect nude mice by using in vivo GFP imaging system.

To examine the utility of the hBMSC-GFP/gelatin scaffold with the pNIPAAm in the wound healing, the skin-defect model of nude mice as showed in FIG. 6 was used and evaluated by the GFP imaging. The original wound as showed in FIGS. 6 (a) and 6 (b) was 3.14 cm² confined by the plastic ring. The in vivo GFP imaging technique was used to analyze the sizes of the skin defects of nude mice in FIGS. 6(b), 6(c) and 6(d) after the transplantation of hBMSC-GFP/gelatin scaffold with pNIPAAm. The green signals of GFP imaging in FIGS. 6(c) and 6(d) were clearly detected in the skin defect of the hBMSC-GFP mice. As showed in FIG. 7 (a), the size of the GFP-positive area at days 3, 7, 14, and 21 were 0.90±0.18, 2.10±0.22, 3.00±0.23, and 3.14±0.25 cm² in the hBMSC-GFP group.

Figure 7:
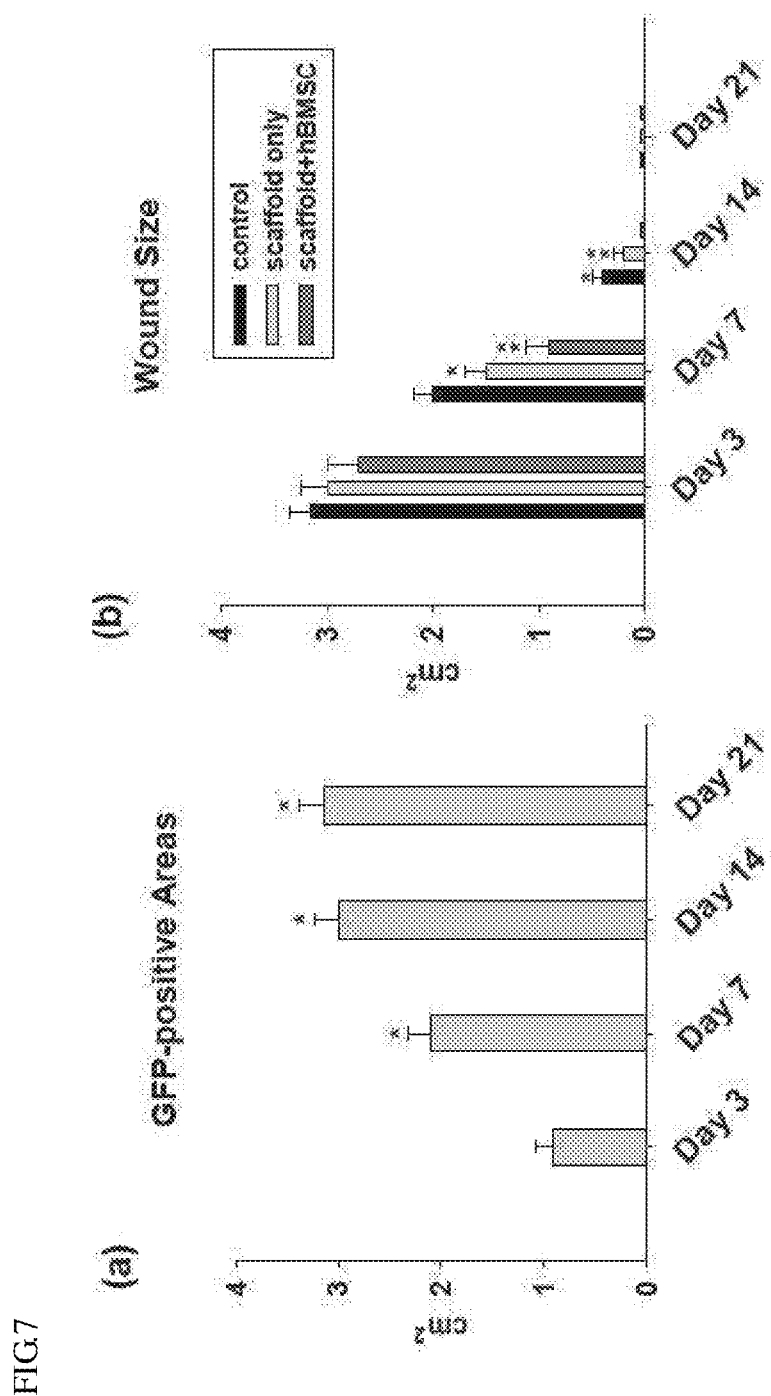
FIG. 7 shows (a) the measurement of GFP-positive areas by using in vivo GFP-positive. (*: $p<0.05$, compared with Day 3) (b) The measurement of skin-defect size. (*: $p<0.05$, **: $p<0.01$, compared with control; control: without any treatment).

As showed in FIG. 7 (b), the wound sizes of all 3 groups were no significantly different among the groups after 3 days of the transplantation [FIG. 7(b)]. At day 7, the wound size of the transplanted hBMSC/gelatin scaffold group decreased to 0.90±0.22 cm² and was significant smaller than the control group (n=12; 2.00±0.19 cm², $p<0.001$) and the scaffold-only group (n=12; 1.50±0.20 cm², $p<0.05$). At Day 14, the wound of the hBMSC group had healed completely. However, the wound size of the control and scaffold-only groups were still having 0.40±0.08 and 0.20±0.09 cm² of skin defects, respectively. At day 21, the wounds in the 3 groups were all healed.

Example 6

Figure 8:
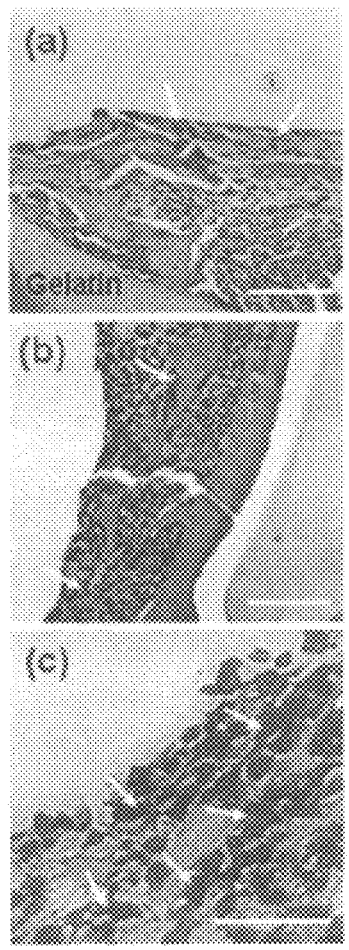
FIG. 8 shows the histology examination of the healed wound performed with the hBMSC-GFP/gelatin scaffold at day 21. Arrow: small vessel (bar: 150 μm).
Figure 8:
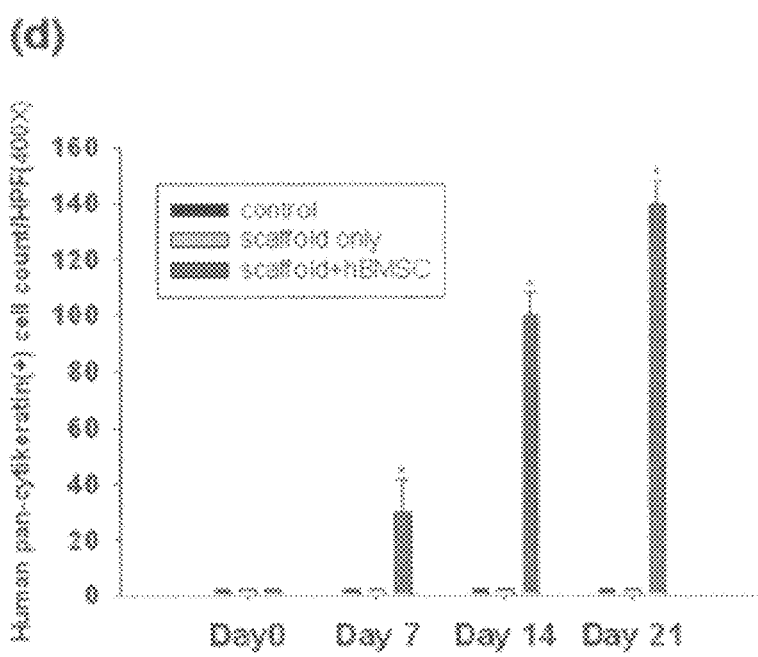
Figure 9:
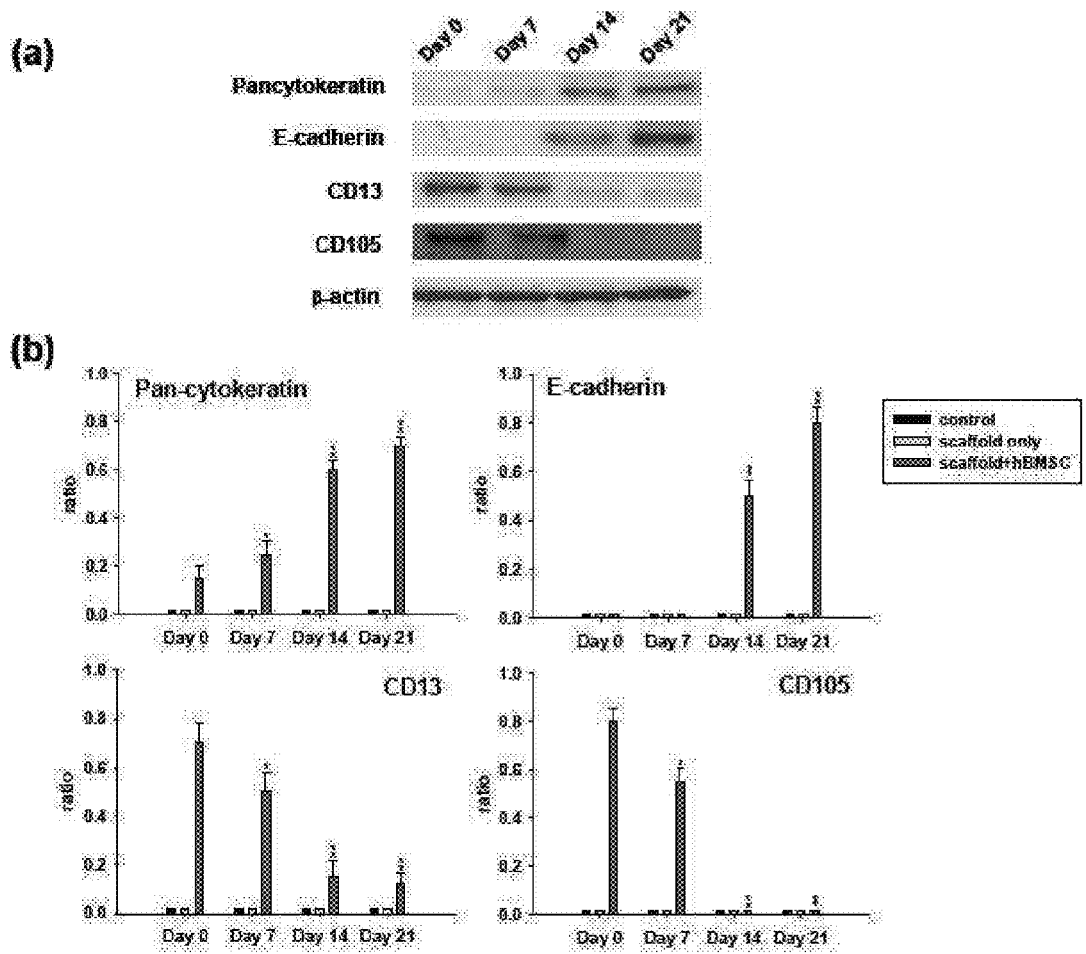
FIG. 9 shows evaluation of human stem cell and cytokeratin markers by western blotting. (a) The protein expressions of human CD13, CD105, pan-cytokeratin, and E-cadherin were measured in the transplanted site of hBMSCs-GFP/gelatin/pNIPAAm-treated mice. (b) The expression ratio of human CD13, CD105, pan-cytokeratin, and E-cadherin in the different treatment groups at Day 0, Day 7, Day 14, and Day 21. (*: $p<0.05$; **: $p<0.01$ compared with day 0).

Histology and Western Blot Assay of hBMSC/Gelatin Scaffold with pNIPAAm and Healing Mice The histology examination of the healed wound was performed with the hBMSC-GFP/gelatin scaffold at day 21. The result indicated in FIG. 8 (a) showed the transplanted cells under the scaffold had formed the epithelium, connect tissues, and small vessels [FIG. 8(a)]. To further characterize the differentiation ability of the transplanted hBMSC, the stem cell markers—human CD13 and human CD105, keratinocyte markers—human pan-cytokeratin and human E-cadherin were evaluated. Compared to the pre-transplantation level, the expression of the human CD13 in the transplanted hBMSC/gelatin scaffold of nude mice significantly decreased and declined at days 7, 14, and 21 in a time-dependent manner. Similarly, the expression of human CD105 in the transplanted site was significantly decreased at days 14 and 21. More importantly, the expressions of human pan-cytokeratin and human E-cadherin as showed in FIGS. 8(b), 8(c) and FIG. 9 (b) were detected in the site of hBMSC/gelatin scaffold and significantly increased at days 7, 14 and 21.

Example 7

Evaluation of Preferred Biodegradable Layer

After testing various mixture of gelatin and glutaraldehyde crosslinking reaction, 2.5% glutaraldehyde, the layer produced by 5% gelatin and 5% type I collagen provided best crosslinking efficacy under lower temperature crosslinking reaction. All reaction was controlled at 4° C. over 36 hours. To further construct the different micro-environments for stem cell growth and differentiation, the gelatin polymer scaffold was made of 5% gel form in warmed DMEM/F12 medium with fibronectin, collagen, laminin, bFGF, or EGF growth factors at 37° C. Due to the special functional group (_NH) in the gelatin gel, it can be further chemically cross-linked with gelatin via cross-linking fibronectin, collagen, laminin, bFGF, or EGF growth factors.

Example 8

Figure 10:
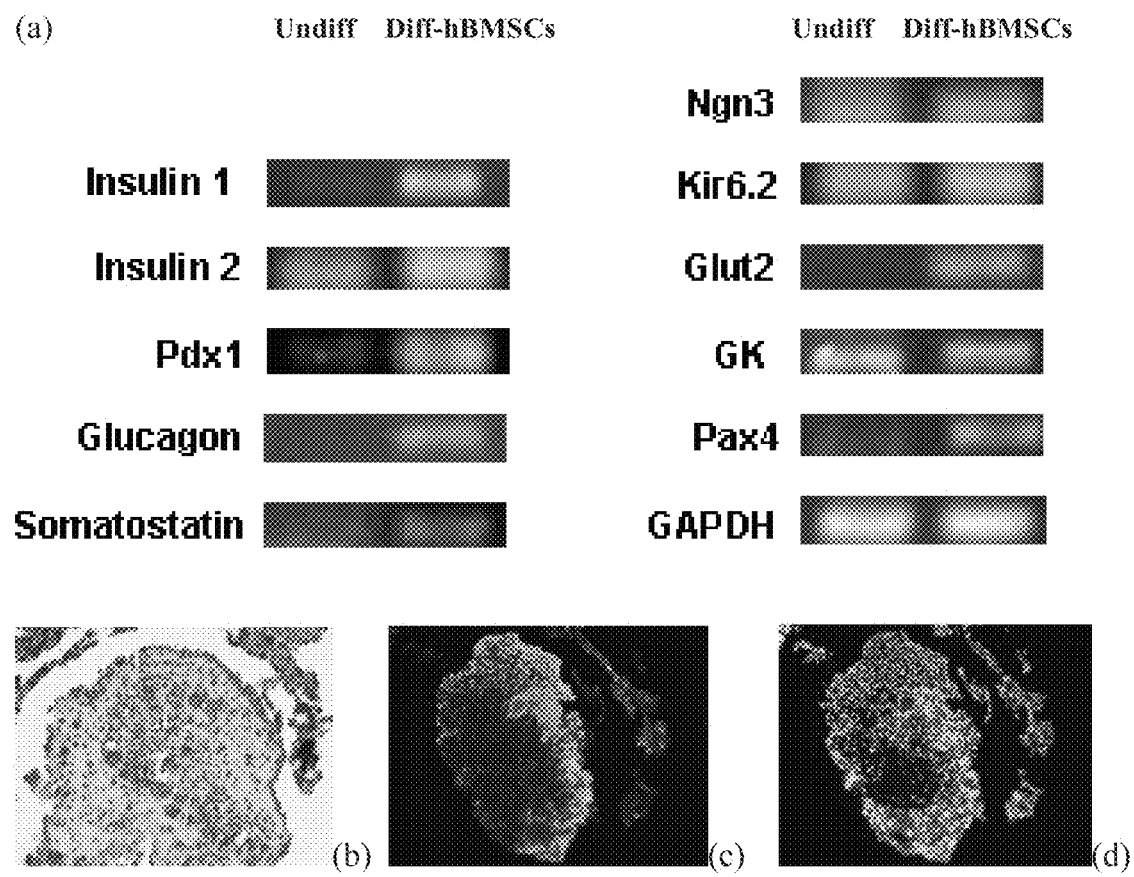
FIG. 10a shows the differentiation of pancreatic stem cells in scaffold by PCR results of the gene expression. The RNA expressions of insulin, glucagon and somatostatin are all detectable in the differentiating hBMSCs, but not observed in undifferentiated hBMSCs.
FIGS. 10b, 10c and 10d show the positive immune reactivity of pancreatic islet markers of insulin, glucagon and somatostatin in the spheroid body of aggregated differentiated hBMSCs by using immunofluorescent staining.

Differentiation of Pancreatic Islet-Like Insulin-Positive Cells Induced by hBMSCs in the Biodegradable Layer of Scaffold Contained with Fibronectin, Laminin, and Type I Collagen hBMSCs cells were cultivated in cell layer in scaffold (contained fibronectin, laminin, and type I collagen), and then added with 10 mL of CMRL 1066 (5.6 mmoL/L glucose, Gibco™, USA) media plus 2% Fetal bovine serum (FBS, Biological Industries, Israel), ITSFn medium (composed: 1:1 of DMEM/F12, 0.6% Glucose, 25 µg/mL Insulin, 100 µg/mL Transferrin, 20 nmoL/L Progesterone, 60 µmoL/L Putrescine, 30 nmoL/L Selenium chloride, 2 mmoL/L Glutamine, 3 mmoL/L Sodium bicarbonate, 5 mmoL/L HEPES buffer, 2 µg/mL Heparin, 20 ng/mL human epidermal growth factor (EGF), 20 ng/mL human basic fibroblastic growth factor (b-FGF) and 20 ng/mL human hepatocyte growth factors, all growth factors were purchased from PerproTech, Israel). After 30 days, the ability of secreting insulin and cell proportion made by hBMSCs in scaffold were examined by immunological staining. As depicted in FIG. 10, PCR results of the gene expression indicated the differentiation of pancreatic stem cells in scaffold. The RNA expressions of insulin, glucagon and somatostatin were all detectable in the differentiating hBMSCs, but not observed in undifferentiated hBMSCs (FIG. 10a). Furthermore, the pancreatic islet markers of insulin (FIG. 10c), glucagon and somatostatin were showed the positive immune reactivity in the spheroid body (FIGS. 10b, 10c and 10d) of aggregated differentiated hBMSCs by using immunofluorescent staining.

Example 9

Figure 11:
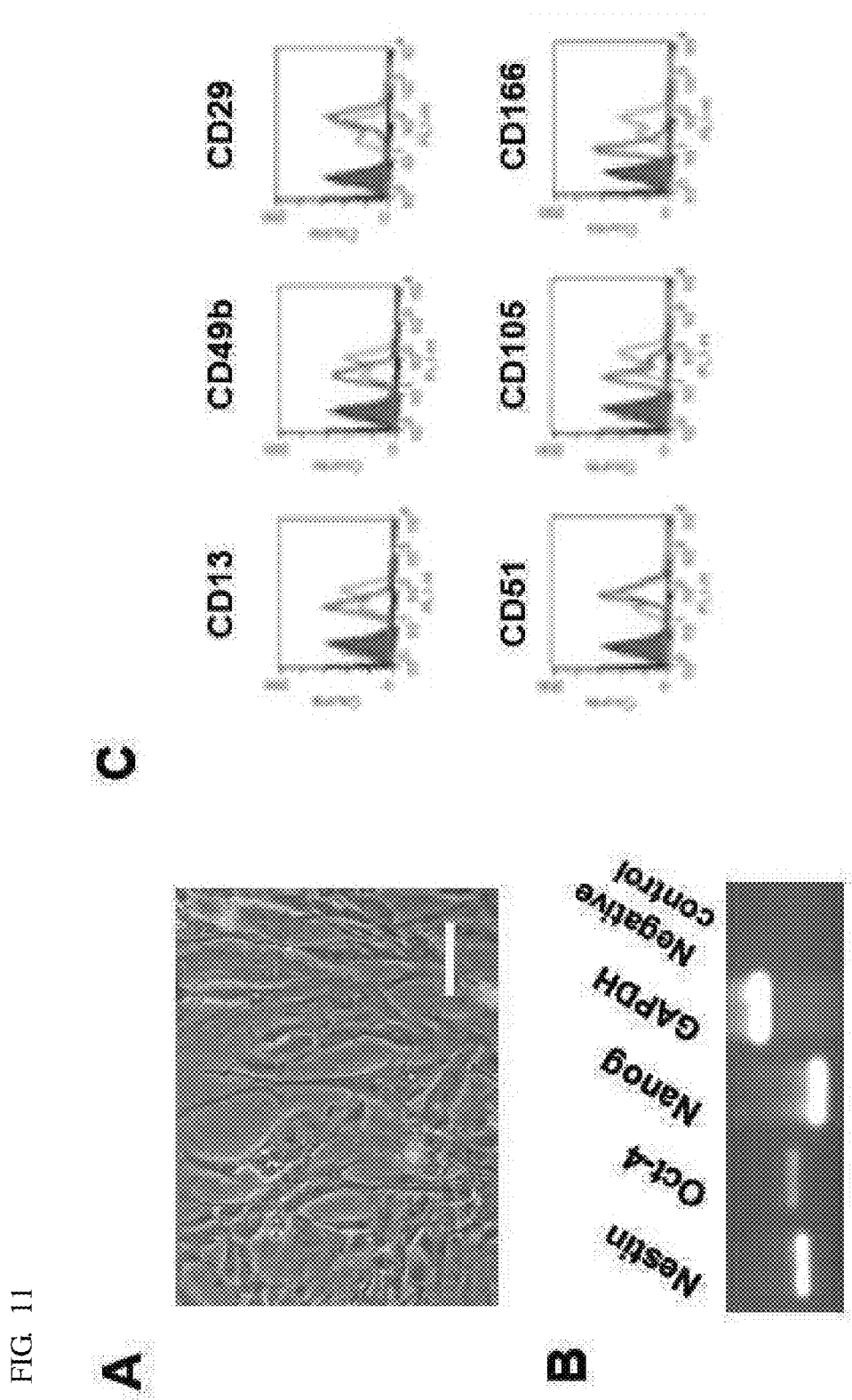
FIG. 11 illustrates induction of placenta-derived multipotent stem cells (PDMSCs) differentiated into insulin- and glucagons-positive cells. In the Figure (a) PDMSCs appeared as spindle-shaped cells with scant cytoplasm and granules around the nuclei; (b) the result showed that PDMSCs positively expressed the mRNA of Nestin, Oct-4, and Nanog; and (C) the flow cytometry analysis for PDMSCs.

Induction of Placenta-Derived Multipotent Stem Cells (PDMSCs) Differentiated into Insulin-Positive Cells This example followed the tenets of the Declaration of Helsinki and informed consent was obtained from the donor subjects. The tissues of human term placenta were dissected and digested by collagenase P (Roche) with HEPES-buffered saline for 7 h at 37° C. The dissociated cells obtained from human placenta were negative for CD45 and glycophorin-A after depletion of CD45⁺ and glycophorin-A⁺ cells by micromagnetic beads (MACS). These cells were then plated in human fibronectin (FN)-coated (5 ng/ml, Sigma) 96-well plates. Expansion medium consisted of Dulbecco's modified Eagle's medium with 1 g/l of glucose (DMEM-LG, Gibco) and 10% fetal bovine serum (FBS; Gibco) supplemented with 10 ng/ml bFGF, 10 ng/ml EGF, 10 ng/ml PDGF-BB (R&D), 100 units/ml penicillin, and 1,000 µg/ml streptomycin, and 2 mM L-glutamine (Gibco). In the example, placenta-derived multipotent stem cells (PDMSCs) were isolated as a follow-up to our previous protocol of negative immunoselection (CD45 and glycophorin-A). PDMSCs usually appeared as spindle-shaped cells with scant cytoplasm and granules around the nuclei (FIG. 11A). Within 7 days, PDMSC cultures were nearly confluent and were passaged 1:3. By using RT-PCR, the result showed that PDMSCs positively expressed the mRNA of Nestin, Oct-4, and Nanog (FIG. 11B). Flow cytometry analysis revealed that PDMSCs were strongly positive (signal; the red line shift right of the control; the solid curve) for CD13, CD29, CD49b, CD51, CD105, and CD166, but were negative for CD45, CD34, MHC I, MHC II, and cKit (FIG. 11C).

Figure 12:
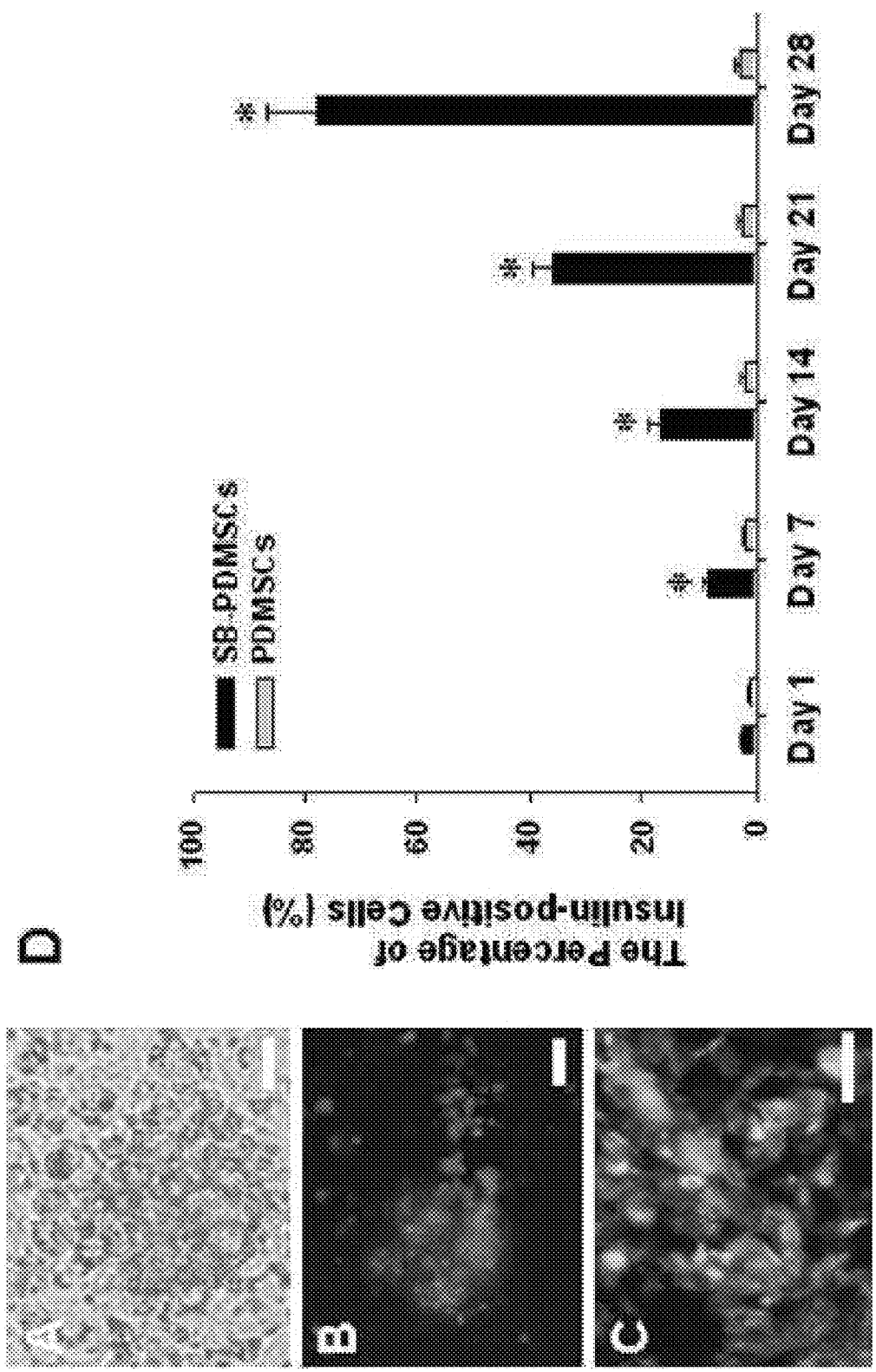
FIG. 12 shows (A) the protein expression of insulin in these spheroid bodies derived from PDMSCs, (B) the numbers of the insulin-positive cells gradually increased in SB-PDMSCs for 4 weeks in pancreatic selection medium culture; (C) both of signals of insulin (red fluorescence) and glucagon (green fluorescence) co-expressed in SB-PDMSCs; and (D) the percentages of insulin-positive cells in PDMSCs.

By using serum-free pancreatic selection medium (DMEM+EGF+bFGF+HGF+ITS) for 4 weeks of culture, a monolayer appeared, and spindle-like PDMSCs gradually formed 3D spheroid-bodies (SB-PDMSCs; FIG. 12A). To further evaluate the protein expression of insulin in these spheroid bodies derived from PDMSCs (SB-PDMSCs; FIG. 12A), immunofluorescent assay was used. The results showed that the numbers of the insulin-positive cells were gradually increased in SB-PDMSCs for 4 weeks in pancreatic selection medium culture (FIGS. 12B and 12D). The pancreatic islet markers of insulin exhibited a high positive rate and percentage of immune reactivity in the spheroid body of aggregated SB-PDMSCs by immunofluorescent staining (FIGS. 12B and 12D). Moreover, both of signals of insulin (red fluorescence) and glucagon (green fluorescence) co-expressed in SB-PDMSCs (FIG. 12C). In contrast, the percentages of insulin-positive cells in PDMSCs (undifferentiated type) were lower and stably expressed in 4-week culture (FIG. 12D).

Figure 13:
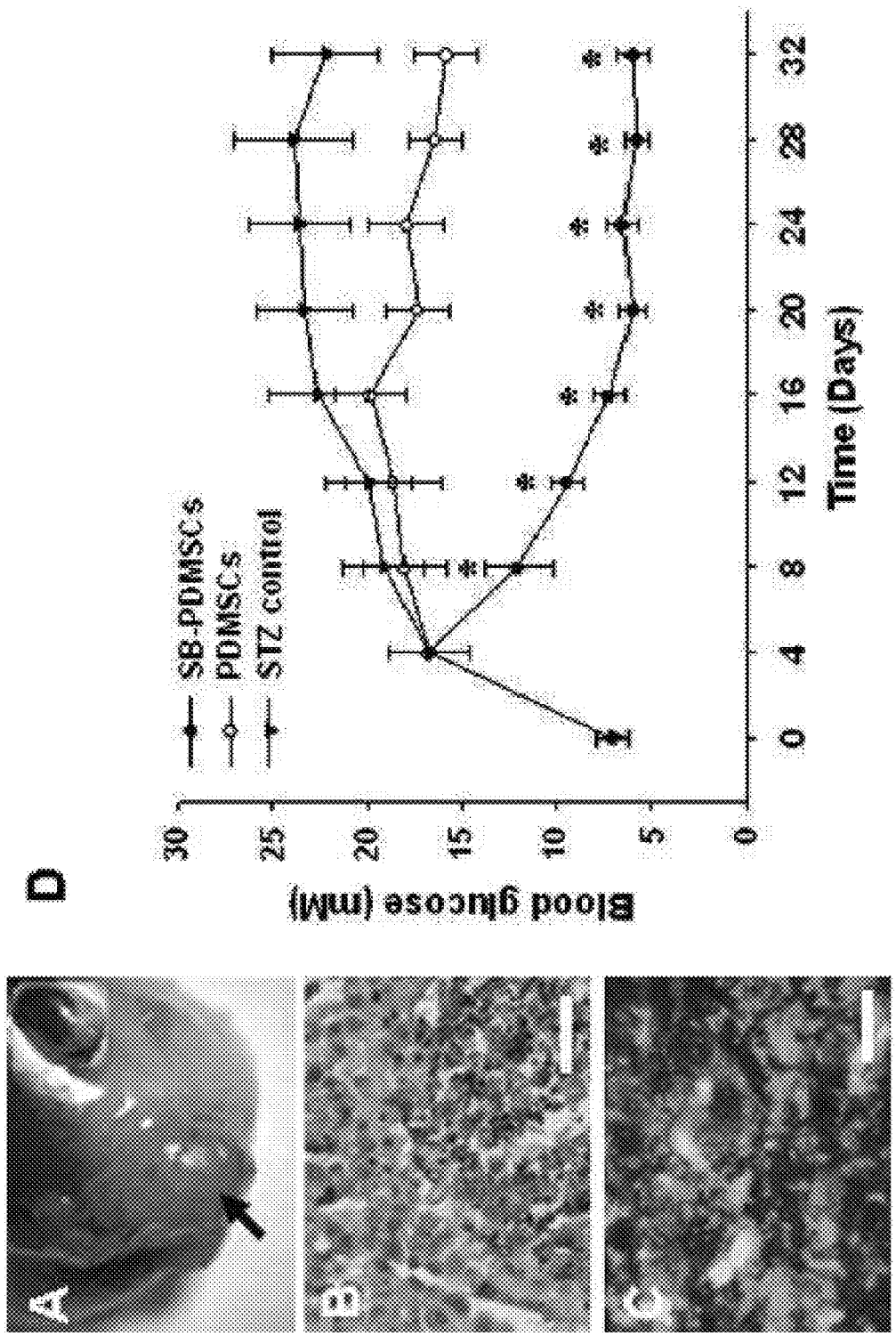
FIG. 13 shows (A) the evidence of the renal subcapsular space in SCID mice providing a microenvironment suitable for endocrine cells differentiation; (B) the result of ex vivo biopsy and histological examination of the transplanted SB-PDMSCs; (C) the immunofluorescent result of insulin (red fluorescence)- and glucagon (green fluorescence)-positive cells in the SB-PDMSC-derived tissues of the subrenal site in SCID mice; and (D) blood glucose examined every two days before and after the transplantation.

SCID mice with STZ pretreatment were employed to examine the restoration of normoglycemia in the differentiated SB-PDMSCs derived from PDMSCs in xenotransplantation. The renal subcapsular space (FIG. 13A) in SCID mice has been demonstrated to provide a microenvironment suitable for endocrine cells differentiation. A total of $2 \times 10^5$ SB-PDMSCs were implanted into the subcapsular space of the left kidney (n=6 each). After 4 weeks, ex vivo biopsy and histological study revealed that transplanted SB-PDMSCs can proliferate and grow solid tissues in the subrenal site (FIGS. 13A and 13B). The immunofluorescent study further confirmed that insulin (red fluorescence)- and glucagon (green fluorescence)-positive cells were detected in the SB-PDMSC-derived tissues of the subrenal site in SCID mice (FIG. 13C). Blood glucose was examined every two days before and after the transplantation (FIG. 13D). Although the blood glucose was reduced in both groups of transplanted animals in comparison to the untreated control group, a significantly lower blood glucose was observed in the group of the SB-PDMSC implanted animals ($p<0.05$; FIG. 13D). The results show that SB-PDMSCs restored the blood glucose to a nearly normal level in the STZ pretreated SCID mice.

Example 10

Figure 14:
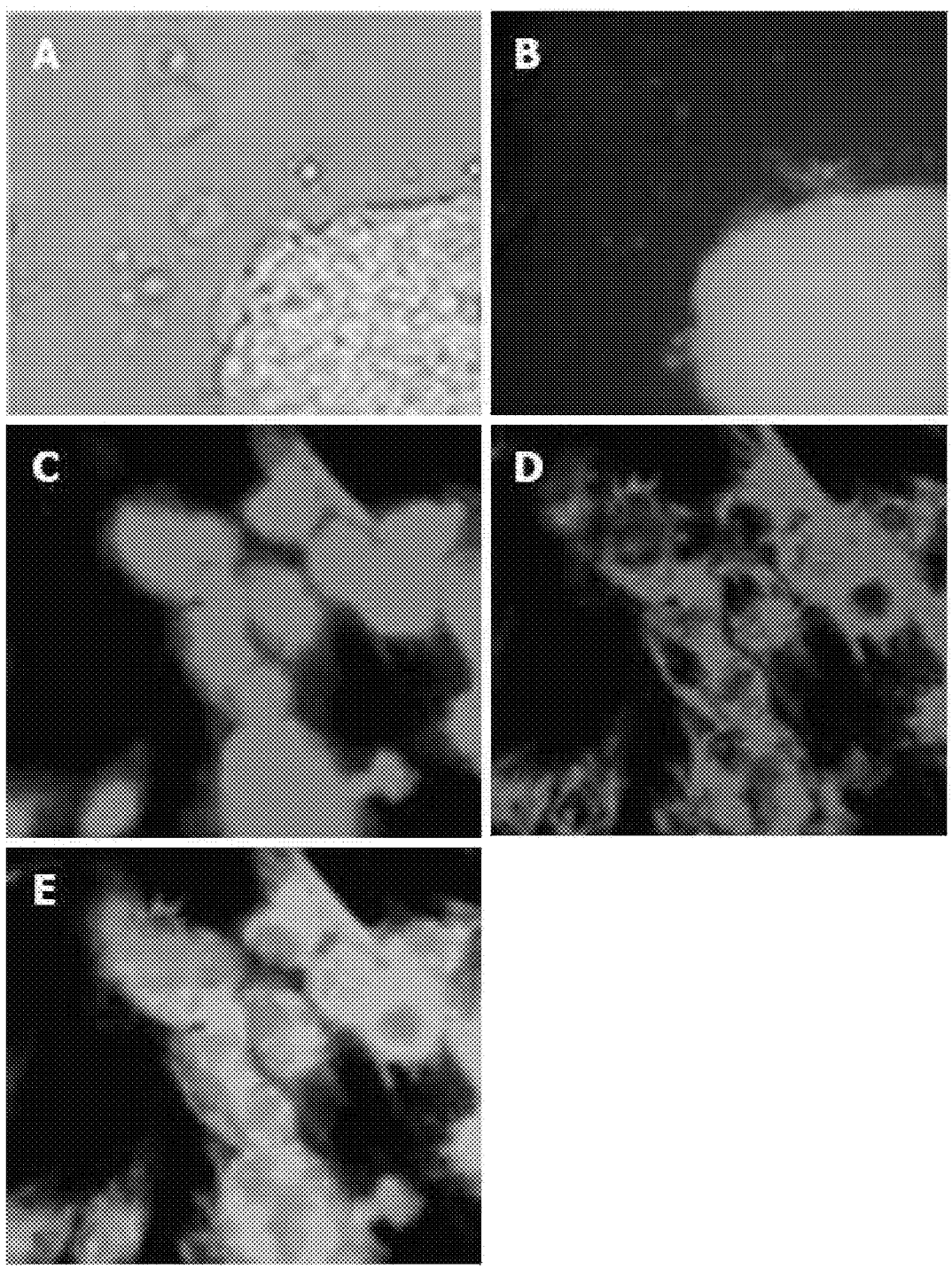
FIG. 14 shows induction of embryonic stem cell differentiated into insulin-positive cells. In this figure, (A) and (B) saturated undifferentiated ES cells as hanging drops by using the medium for undifferentiated ES cells without LIF supplement; (C) the result of the positive signals for glucagon (green color); (D) insulin (red color); and (E) immunofluorescent assay (merged imaging) after induction.

Induction of Embryonic Stem Cell Differentiated into Insulin- and Glucagons-Positive Cells The murine embryonic stem cell strain of BALB/c mice (ESC26GJ constructed by Chiou et al during passages 25 and 50 was used in the present study). This strain that has been transferred by pCX-EGFP can express green fluorescence constitutively. Undifferentiated murine stem cells were cultured on mitomycin C-treated STO (mouse embryonic fibroblast cell line, ATCC CRL-1503 passages 15-35 were utilized) and supplied to Dulbecco's modified Eagle's medium (DMEM, 4500 mg glucose/L) containing 15% fetal bovine serum (FBS, HyClone defined and tested batches or ES cell grade), 1% nonessential amino acid, 0.1 mmol/L β-mercaptoethanol, 100 U/mL penicillin, 100 μg/mL streptomycin (all from GIBCO-BRL) and leukemia inhibitory factor (LIF, R&D). Cells were cultured in a humidified chamber containing a 5% $CO_2$/air mixture at 37° C., subcultured every 3 d and changed medium twice a day. Alkaline phosphatase detection kit (Chemicon) was utilized to examine the quality of undifferentiated ES every 5 passages. Approximately 70% saturated undifferentiated ES cells were harvested and aggregated as hanging drops with the density of 3000 cells/per drop for 4 d (using the medium for undifferentiated ES cells without LIF supplement; FIGS. 14A and 14B). To further induce ES cells differentiated into insulin-positive cells, the new serum-free ITSFn medium (composed: 1:1 of DMEM/F12, 0.6% Glucose, 25 μg/mL Insulin, 100 μg/mL Transferrin, 20 nmoL/L Progesterone, 60 μmoL/L Putrescine, 30 nmoL/L Selenium chloride, 2 mmoL/L Glutamine, 3 mmoL/L Sodium bicarbonate, 5 mmoL/L HEPES buffer, 2 μg/mL Heparin, 20 ng/mL human epidermal growth factor (EGF), 20 ng/mL human basic fibroblastic growth factor (b-FGF) and 20 ng/mL human hepatocyte growth factors were used and place on new dish. After 28 induction, the positive signals for glucagon (green color; FIG. 14C) and insulin (red color; FIG. 14D) were detected by immunofluorescent assay (FIG. 14E; merged imaging).

Example 11

Differentiation of Neural Cells Induced by Using Cultivated Neural Stem Cells in Scaffold Contained Basic Fibroblast Growth Factor (bFGF)

Figure 15:
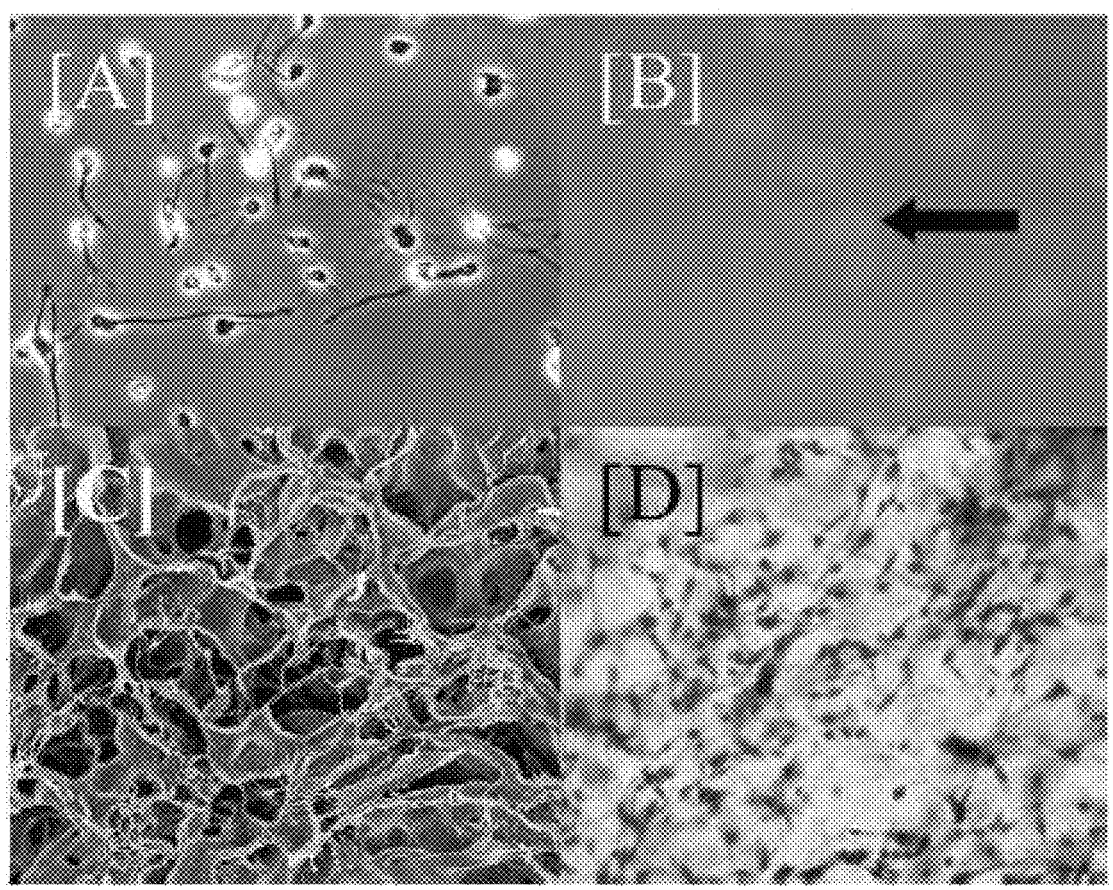
FIG. 15 shows (A) the hNSCs and (B) neurospheres (solid arrow) seeded thereafter into the medium with gelatin scaffold; (C) after five passages; (D) the growth and development of these hNSCs in gelatin scaffold reviewed by H&E; and (E) hNSCs proliferation ability of three cases in different conditions, (F) Dot blot hybridization to examine the MAP2 gene expression in scaffold. Equal total RNA (20 ug) was used for each examination, (G) Dot blot hybridization to examine the NeuN gene expression in scaffold. Equal total RNA (20 ug) was used for each examination.
Figure 15:
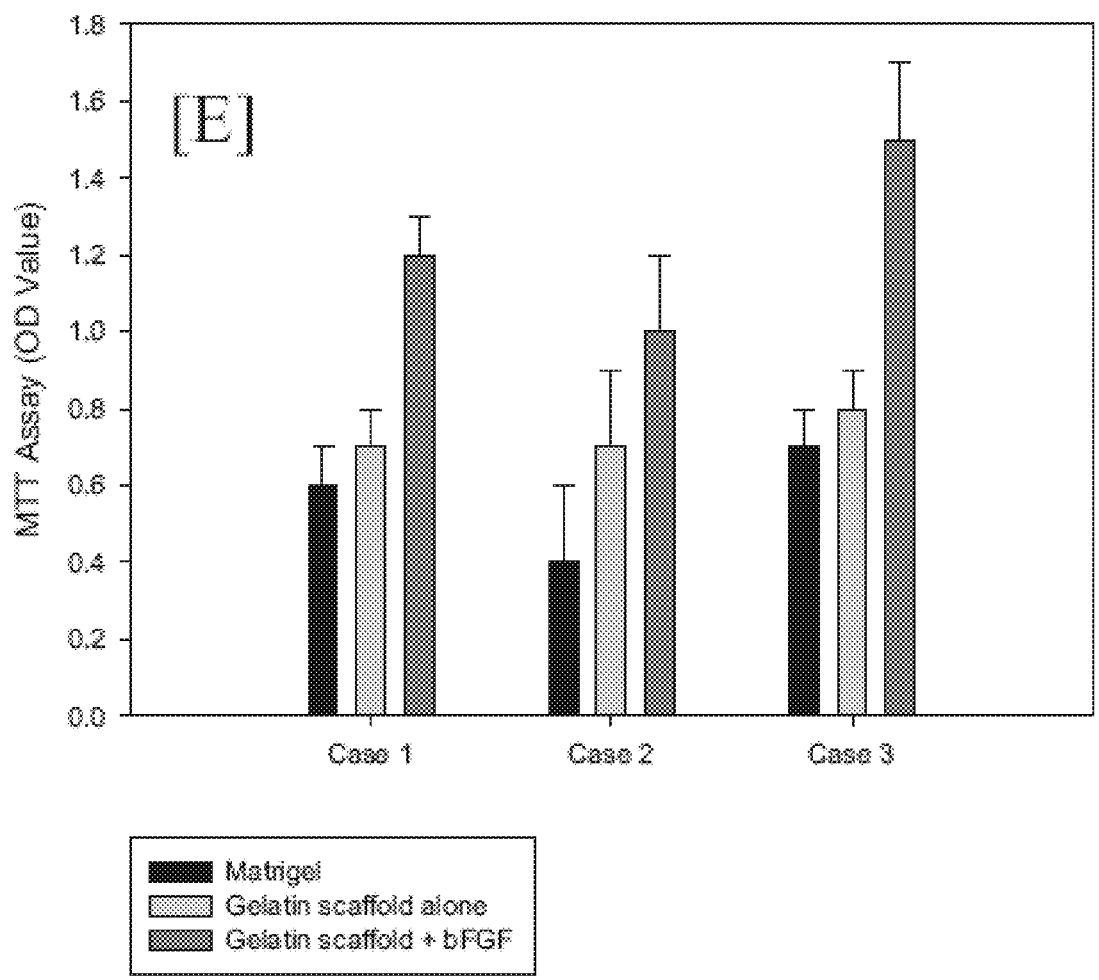

The human neural stem cell (hNSC) could be a useful donor tissue for neural regeneration by transplantation after central nervous system damage and spinal injury. However, the difficulty in ex vivo cell culture with this biomaterial graft is still unsolved: hNSC cannot develop and differentiate well in conventional two-dimensional culture media. More recent studies have focused on biodegradable material, such as gelatin scaffolds, to provide better adhesion and growth for hNSC before transplantation. Herein, gelatin polymer scaffolds coated with basic fibroblast growth factor (bFGF) were used to form a three-dimensional structure of hNSCs. Tissues from the lateral ventricle wall were dissociated and incubated in HBSS containing collagenase for 10 minutes at 37° C. 4 Dissociated cells were then centrifuged at 150 g for 5 minutes. The enzyme solution was removed and replaced with serum-free culture media composed of DMEM (GIBCO) and F-12 nutrient (1:1), including bFGF (10 ng/mL, R&D Systems), Hepes buffer (5 mmol), glucose (0.6%), sodium bicarbonate (3 mmol), and glutamine (2 mmol). After 2 week culture, some stem cells (FIG. 15A) aggregated and formed spheroid-like bodies, called neurospheres. These neurospheres (FIG. 15B) were obtained in suspension and cultivated them by seeding into gelatin scaffolds (FIG. 15C). The gelatin polymer scaffold (Sigma, Type A, powder) was made of 5% gel form in warmed DMEM/F12 medium with bFGF at 37° C. Due to the special functional group (_NH) in the gelatin gel, it can be further chemically cross-linked with gelatin via cross-linking bFGF growth factor. We observed that gelatin scaffolds provided a good microenvironment for the adhesion and growth of hNSCs to form neural network-like structures. Upon morphologic analysis, the scaffold may also help the proliferation and differentiation of hNSCs to become neurons. By MTT assay, better cell proliferation was found in the group when bFGF (EGF) was coated in gelatin scaffold as well (FIG. 15E). Gelatin polymer scaffolds were coated with basic fibroblast growth factor (bFGF) to form a three-dimensional structure of hNSCs. This example provides a potential new cell transfer technology. Nontoxic and biodegradable gelatin scaffolds coated with bFGF formed a three-dimensional microenvironment facilitating proliferation and differentiation of hNSCs before transplantation.

Example 12

Figure 16:
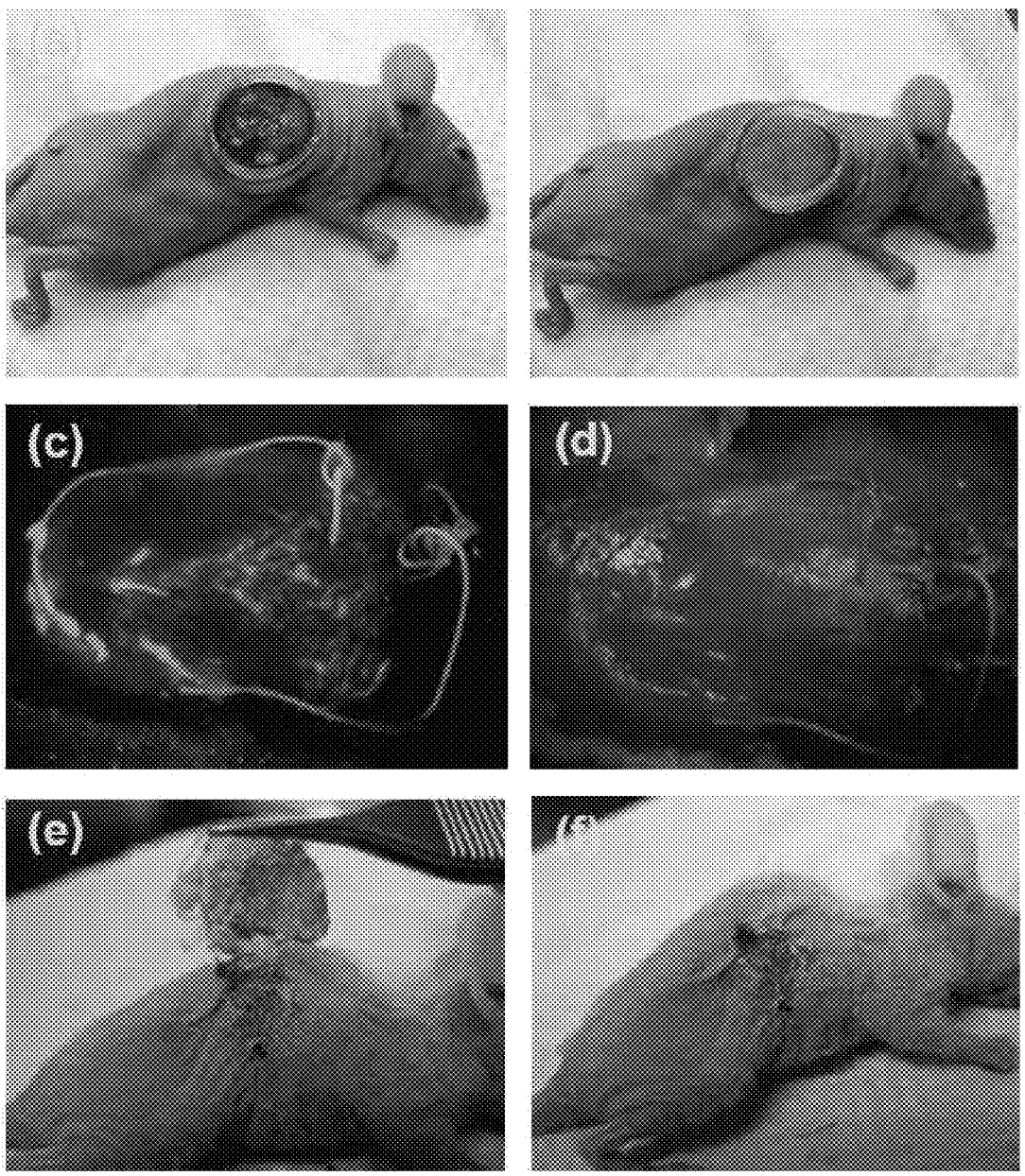
FIG. 16 shows (A) original wound; (B) original wound confined by plastic ring; (C) the recovery of wound under natural light, (D) the recovery of wound under in vivo fluorescent microscopy; (E) the condition of outer layer of thermo-sensitive scaffold being peeled after treatment of cold water; and (F) the recovery of wound in nude mice.
Figure 17:
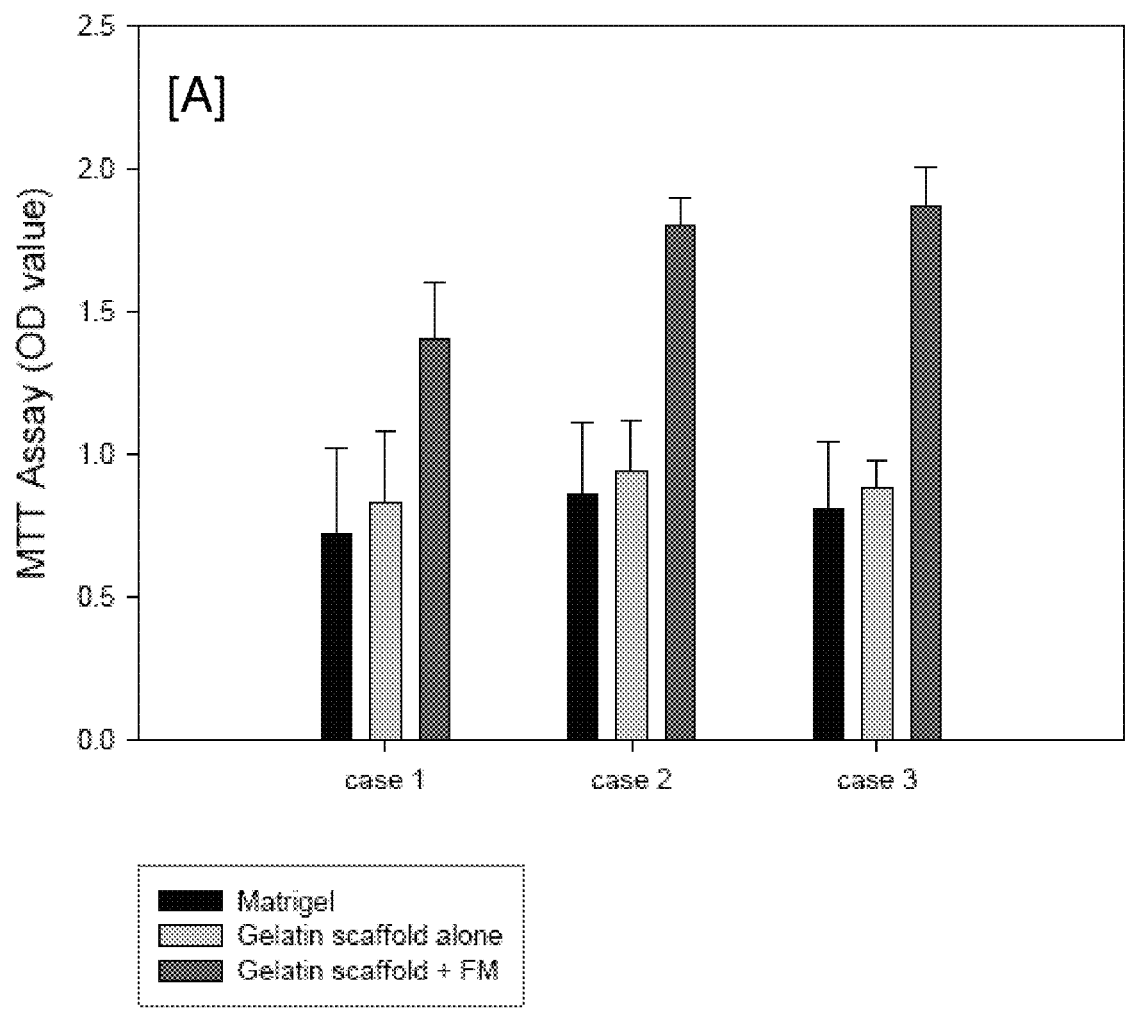
FIG. 17 shows the proliferation and differentiation of dermis derived stem cells matrixgel, scaffold alone or scaffold with formulated medium (FM). In this figure, (A) The MTT assays were used to evaluate the cells proliferation ability of three cases in different conditions, (B) Dot blot hybridization to examine the E-cadherin gene expression in scaffold. Equal total RNA (20 ug) was used for each examination, (C) Dot blot hybridization to examine the keratin gene expression in scaffold. Equal total RNA (20 ug) was used for each examination.

Examination on Temperature-Sensitive Biological Transplanted Scaffold in in vivo Animal Fluorescent Cells As showed in FIG. 16, eight-week-old nude mice were anesthetized by 40 mg/kg pentobarbital intraperitoneal injection. Around 2 cm diameter of trauma was made on the back of the mice. After inserting into the trauma with hBMSCs-GFP (stem cell constitutively expressed green fluorescent protein gene) cultivated in temperature-sensitive biological transplanted scaffold over 3 weeks, trauma periphery was blocked by plastic circle to avoid causing epithelialization (FIGS. 16a and 16b). Skin regeneration in body was examined by fluorescent in vivo monitoring system. The results of GFP imaging were consistent with the clinical observation and histology survey (FIGS. 16e and 16f). The excitation filter of 470 nm with a lamp supply of optical lighting of 150 watts (Southern California Services, USA) was used as an excited light source (470 nm) to project on the foci of the GFP-positive cells of the living mice and ex vivo transplanted tissues. The GFP imaging capture and photography is based on the record of the digital camera (Olympus) through optical configuration of dissected microscope (SZ60; Olympus) with a 515 nm viewing (emission) filter. Furthermore, the hBMSC group mice received the in vivo GFP imaging evaluation, and results showed that the GFP-positive signals (FIG. 16c) were significantly detected in the regenerated skin tissues with transplanted the scaffold with hBMSCs-GFP (FIGS. 16c and 16d).

Herein it demonstrated the incorporation of GFP reporter gene into the genome of hBMSC as markers of proliferation both in cells and in living animals. Without adding any exogenous substrates or antibodies, the constitutive GFP signals at the living cellular level as well as in vivo transplanted graft could be visualized directly and quickly under specific excitation wavelength for noninvasive, real time, and in situ observation. In addition, in vitro and in vivo GFP imaging systems provide a new imaging modality for understanding the differentiation process and the effective expression of stem cell in wound healing.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for treating a patient with a skin defect, consisting of:
    (a) providing said patient with a composite consisting of an N-isopropylacrylamide (NIPAAm) layer polymerized with a) a biodegradable layer and b) a layer of polypropylene (PP) non-woven, wherein said biodegradable layer consists of gelatin and a glutaraldehyde crosslinking agent, and wherein a bone marrow derived mononuclear cell with CD45 negative and glycophorin A negative is cultivated on and is present on the biodegradable layer;
    (b) covering the skin defect of the patient with said composite; and
    (c) treating the composite with water below 25° C. to strip off the layer of polypropylene (PP) non-woven;
    wherein the skin defect is a wound resulting from trauma or burn injury.

2. The method of claim 1, wherein the bone marrow derived mononuclear cell with CD45 negative and glycophorin A negative has the capacity to differentiate into epithelium, connective tissue and small vessels.

3. The method of claim 1, wherein the bone marrow derived mononuclear cell is cultivated and present on the biodegradable layer for 2 to 3 weeks.

4. The method of claim 1, wherein the skin defect of the patient is covered with the composite for 3 to 21 days.

* * * * *